United States Patent
Pope et al.

(10) Patent No.: US 11,660,257 B2
(45) Date of Patent: May 30, 2023

(54) PARTICULATE AEROGEL MATERIAL KIT FOR GRIP ENHANCEMENT

(71) Applicant: Chalkless LLC, Wilmington, MA (US)

(72) Inventors: David G. Pope, West Newbury, MA (US); James M. Pidhurney, Auburn, NH (US); Stephen A. Steiner, III, Milwaukee, WI (US); Moriah C. Buckwalter, South Weymouth, MA (US); Ryan T. Nelson, Fort Collins, CO (US)

(73) Assignee: Chalkless, Inc., Wilmington, DE (US)

( * ) Notice: Subject to any disclaimer, the term of this patent is extended or adjusted under 35 U.S.C. 154(b) by 0 days.

(21) Appl. No.: 17/810,356

(22) Filed: Jul. 1, 2022

(65) Prior Publication Data

US 2023/0000730 A1    Jan. 5, 2023

Related U.S. Application Data

(60) Provisional application No. 63/217,686, filed on Jul. 1, 2021.

(51) Int. Cl.
| | | |
|---|---|---|
| A61K 8/02 | (2006.01) | |
| B65D 83/06 | (2006.01) | |
| B65D 83/00 | (2006.01) | |

(52) U.S. Cl.
CPC ........ *A61K 8/0241* (2013.01); *B65D 83/0055* (2013.01); *B65D 83/06* (2013.01)

(58) Field of Classification Search
CPC ...... A61K 8/0241; A61K 8/25; A61K 8/8126; B65D 83/0055; B65D 83/66; B65D 83/06; B65D 83/0805; B65D 2203/06; B65D 47/043
USPC ........................... 222/632, 635, 92–107, 190
See application file for complete search history.

(56) References Cited

U.S. PATENT DOCUMENTS

| | | | |
|---|---|---|---|
| 2004/0121156 A1* | 6/2004 | Meyer .................. | C09C 1/3072 427/446 |
| 2013/0037563 A1* | 2/2013 | Steele ................ | B65D 47/2043 222/530 |
| 2015/0374098 A1* | 12/2015 | Albisetti .................. | A61K 8/26 222/206 |
| 2017/0238676 A1* | 8/2017 | Valverde .............. | A61K 8/8158 |
| 2020/0405596 A1* | 12/2020 | Dillon ...................... | A61K 8/25 |

FOREIGN PATENT DOCUMENTS

CA            2565268        *   4/2007

OTHER PUBLICATIONS

International search report and opinion for PCT/US22/73334.

\* cited by examiner

*Primary Examiner* — Lien M Ngo
(74) *Attorney, Agent, or Firm* — Talus Law Group LLC

(57) ABSTRACT

Particulate aerogel material kit for grip enhancement, and related systems and methods, are generally described. Certain embodiments are related to interfaces comprising human skin, a layer of particulate aerogel material, and a solid surface. Methods of creating such interfaces, packaging the particulate aerogel material, and applications thereof (including kits for grip enhancement) are also described.

26 Claims, 22 Drawing Sheets

PARTICULATE AEROGEL MATERIAL KIT FOR GRIP ENHANCEMENT

CROSS REFERENCE TO RELATED APPLICATIONS

This application claims the benefit of U.S. Provisional Patent App. No. 63,217/686 entitled "Particulate Aerogel Material for Grip Enhancement" and filed on Jul. 1, 2021, the entire contents of which is incorporated herein by reference in its entirety for all purposes.

TECHNICAL FIELD

Particulate aerogel material for grip enhancement, and related systems and methods, are generally described.

SUMMARY

Particulate aerogel material for grip enhancement, and related systems and methods, are generally described. Certain embodiments are related to interfaces comprising human skin, a layer of particulate aerogel material, and a solid surface. Methods of creating such interfaces, packaging the particulate aerogel material, and applications thereof (including grip enhancement) are also described. The subject matter of the present disclosure involves, in some cases, interrelated products, alternative solutions to a particular problem, and/or a plurality of different uses of one or more systems and/or articles.

In some embodiments, a method is provided. The method comprises, in some embodiments, establishing direct contact and/or indirect solid contact between human skin, a particulate aerogel material, and a solid surface, wherein the particulate aerogel material is between the human skin and the solid surface.

In certain embodiments, an article is provided. In some embodiments, the article comprises a flexible container; and a particulate aerogel material within the container. In some embodiments, at least a portion of a boundary of the container is porous and permits transport of the particulate aerogel through the porous boundary upon application of force to the flexible container.

In certain embodiments, the article comprises a container; and particulate aerogel material within the container; wherein the container comprises a plurality of openings through which the particulate hydrophobic aerogel material can be transported.

In some embodiments, the article comprises a fibrous matrix; and particulate aerogel material associated with the fibrous matrix; wherein the combination of the fibrous matrix and the particulate aerogel material is in the form of a sheet.

In some embodiments, the article comprises a container; and a plurality of sheets within the container; wherein each of the sheets comprises a fibrous matrix; and particulate aerogel material associated with the fibrous matrix.

In certain embodiments, a material is provided. In some embodiments, the material comprises a liquid; and particulate aerogel material dispersed within the liquid.

In certain embodiments, a kit is provided. In some embodiments, the kit comprises a liquid; and particulate aerogel material; wherein, when the liquid and the particulate aerogel material are combined, the particulate aerogel material and the liquid form a combination that enhances friction between human skin and solid surfaces.

In certain embodiments, a combination is provided. The combination comprises, in some embodiments, human skin; particulate aerogel material in contact with the human skin; and a solid surface in contact with the particulate aerogel material.

Other advantages and novel features of the present disclosure will become apparent from the following detailed description of various non-limiting embodiments of the disclosure when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present disclosure will be described by way of example with reference to the accompanying figures, which are schematic and are not intended to be drawn to scale unless otherwise indicated. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure.

DETAILED DESCRIPTION

Figure 1:
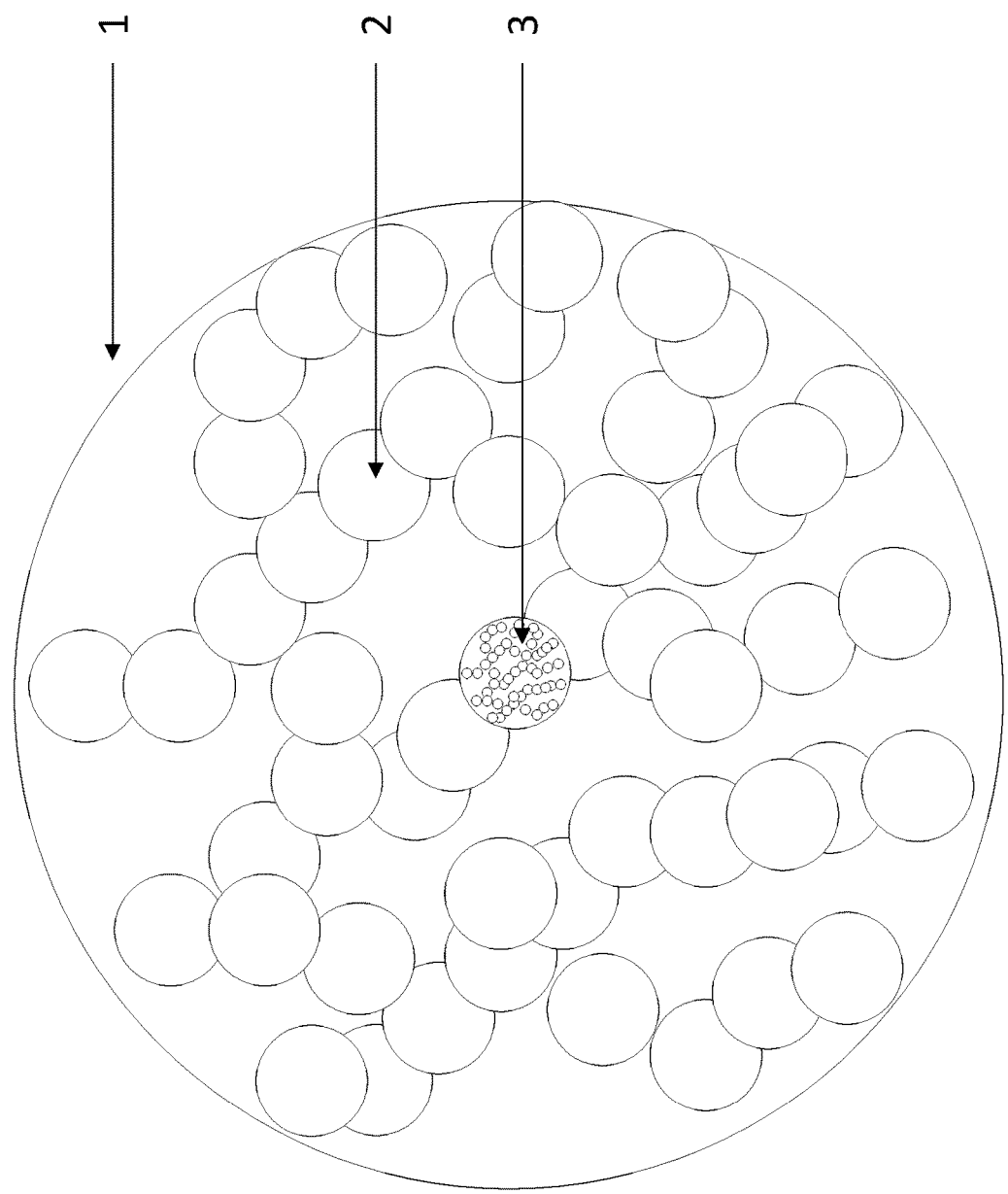
FIG. 1 depicts a magnified view of an aerogel particle, according to certain embodiments.

Gripping is a natural part of human interaction with solid surfaces. In some instances, humans must grip an object. In other instances, humans must temporarily grip against a surface. Gripping is often impeded by perspiration, natural oil secretion, smoothness of skin, and/or the surface to be gripped or gripped against and moisture/oil from the environment. Improving the friction between human skin and solid surfaces is thus desirable for improving grip. The present disclosure provides methods and materials useful for improving human grip. In some embodiments, particulate aerogel material is applied to human skin resulting in improved grip with solid surfaces. In other instances, particulate aerogel material is applied to a solid surface to be gripped resulting in improved grip. In some embodiments, particulate aerogel material is applied to an exterior surface of a glove, footwear, or other apparel to improve grip. In some embodiments, the particulate aerogel material provides improved tribological, absorptive, antiperspirant, textural or surface area properties.

The inventors have observed the unexpected result that applying particulate aerogel material to human skin results in improved grip between said human skin and a solid surface. In some embodiments, the particulate aerogel material forms an interface between the human skin and the solid surface.

In some embodiments the particulate aerogel material increases the coefficient of friction between the human skin and the solid surface and/or between a surface of a material with which the human skin is in contact (either directly or via indirect solid contact) and the solid surface. In some embodiments, the particulate aerogel material increases the coefficient of friction between the human skin and the solid surface by at least 1%, at least 5%, at least 10%, at least 20%, at least 30%, at least 40%, or at least 50% relative to the coefficient of friction in the absence of the particulate aerogel material. In some embodiments, the particulate aerogel material increases the coefficient of friction between a surface that is in contact with (either directly or via indirect solid contact) human skin (e.g., the exterior surface of a glove being worn on a hand) and a solid surface by at least 1%, at least 5%, at least 10%, at least 20%, at least 30%, at least 40%, or at least 50% relative to the coefficient of friction in the absence of the particulate aerogel material. In some embodiments the particulate aerogel material provides an antiperspirant function. In some embodiments the particulate aerogel material provides an antiperspirant function by blocking pores in the human skin and/or absorbing excreted perspiration from human skin. In some embodiments, natural oils found on human skin are at least partially absorbed by the particulate aerogel material resulting in adhesion of the particulate aerogel material to the skin. In some embodiments, the particulate aerogel material repels water, serving as a water-repellant or water-proof layer on human skin and/or between a surface of a material with which the human skin is in contact (either directly or via indirect solid contact) and the solid surface.

In some embodiments the particulate aerogel material exhibits a high surface area. In some embodiments, the particulate aerogel material exhibits a surface area of at least 100 $m^2/g$, at least 200 $m^2/g$, at least 300 $m^2/g$, at least 400 $m^2/g$, at least 500 $m^2/g$, at least 600 $m^2/g$, at least 700 $m^2/g$, at least 800 $m^2/g$, at least 900 $m^2/g$, at least 1000 $m^2/g$, at least 1100 $m^2/g$, or at least 1200 $m^2/g$. In some embodiments, the presence of the particulate aerogel material in contact with human skin increases the surface area available for gripping. In some embodiments, the particulate aerogel material has a high surface roughness resulting in increased texture over the human skin. In some embodiments, these functions and/or a combination of these functions results in improved grip between the human skin and the solid surface and/or improved grip between a surface of a material with which the human skin is in contact and the solid surface.

In some embodiments, the particulate aerogel material exhibits a highly porous structure. In some embodiments, the particulate aerogel material exhibits a BJH pore volume of greater than or equal to 0.05 $g/cm^3$, greater than or equal to 1 $g/cm^3$, greater than or equal to 2 $g/cm^3$, greater than or equal to 3 $g/cm^3$, greater than or equal to 4 $g/cm^3$, or less than or equal to 5 $g/cm^3$. In some embodiments, the particulate aerogel material exhibits a small pore size. In some embodiments, the particulate aerogel material exhibits a BJH average pore width of less than 10 nm, less than 20 nm, less than 30 nm, less than 40 nm, less than 50 nm, less than 60 nm, less than 70 nm, less than 80 nm, less than 90 nm, less than 100 nm, less than 500 nm, less than 1 µm, less than 10 µm, less than 100 µm, or less than 1 mm. In some embodiments, the high pore volume of the particulate aerogel material results in good sorption. In some embodiments, the small pore size of the particulate aerogel material results in efficient capillarity driven wetting of natural oils found on human skin, and/or perspiration.

Solutions that currently exist to improve grip include chalk, antiperspirant, and gloves. Chalk will provide transient grip enhancement; however, it does not prevent sweating, is messy, marks surfaces, is not highly porous, and is easily washed off due to its hydrophilic nature. Antiperspirant will help to reduce sweating from human skin, but it does not improve the surface area of the skin or remove moisture that is already present. Gloves and other types of apparel can help to improve grip; however, they are not always suitable or permitted in every application. Gloves can also impede the desired action by reducing dexterity or increasing the diameter of the object being gripped. Even in circumstances where gloves are permitted, they can be impeded by the presence of moisture and/or be ineffective in gripping against smooth surfaces.

In some embodiments, establishing direct contact and/or indirect solid contact between human skin, a particulate aerogel material, and a solid surface, wherein the particulate aerogel material is between the human skin and the solid surface, will increase the friction between the human skin and the solid surface. Without wishing to be bound by any particular theory, it is believed that the particulate aerogel material increases friction between human skin and a solid surface by both increasing the surface area between the solid surface and the human skin as well as absorbing oil or sweat that might be present on the human skin. In some embodiments, the human skin is on a foot (e.g., on the bottom of a foot). In some embodiments, the human skin is on a hand (e.g., on the inside of the hand, such as on the palm of a hand and/or interior surfaces of digits of the hand). In some embodiments, the human skin is on an arm. In some embodiments, the human skin is on a leg. In some embodiments, the human skin is on a torso. In some embodiments, the human skin is on a face. In other embodiments, the human skin is on a back.

In some embodiments, human skin is first contacted with the particulate aerogel material (e.g., to establish direct contact or indirect solid contact between the human skin and the particulate aerogel material) and then a solid surface is contacted with the particulate aerogel material that is in contact with the human skin (e.g., to establish direct or indirect solid contact between the solid surface and the particulate aerogel material).

In some embodiments, a solid surface is first contacted with the particulate aerogel material (e.g., to establish direct or indirect solid contact between the solid surface and the particulate aerogel material) and then human skin is contacted with the particulate aerogel material that is in contact with the solid surface (e.g., to establish direct contact or indirect solid contact between the human skin and the particulate aerogel material).

In some embodiments, the human skin is in direct contact with the particulate aerogel material. In some embodiments, the human skin is touching the particulate aerogel material with no solid material (e.g., a solid layer) in between the human skin and the particulate aerogel. For example, in FIG. 10A, particulate aerogel material 4 is in direct contact with human skin 18.

In some embodiments, the human skin is in indirect solid contact with the particulate aerogel material. Two solid objects are said to be in "indirect solid contact" when there are one or more solid materials between them and at least one pathway can be traced from the first solid object to the second solid object that passes only through solid materials. As one example, if a hand is inside a glove and particulate aerogel material is applied to the external surface of the glove, the hand and the particulate aerogel material would be said to be in indirect solid contact because a pathway can be traced from the hand, through the glove (a solid object) and to the particulate aerogel material. Two solid objects are said to be in "direct contact" when they are in direct physical contact with each other. As one example, in FIG. 10E, particulate aerogel material 4 is in indirect solid contact with human skin 18 because solid layer 22 is in direct contact with both human skin 18 and particulate aerogel material 4.

It is possible for two objects to be both in direct contact with each other and in indirect solid contact with each other, for example, when there is an intervening solid material or materials at one portion of the interface between the objects and direct contact between the objects at another portion of the interface between the objects.

In some embodiments in which the human skin and the particulate aerogel are in indirect solid contact, the material between the human skin and the particulate aerogel is in the form of a layer. For example, in FIG. 10E, layer 22 is present between human skin 18 and particulate aerogel material 4. In some embodiments the layer has a thickness of less than 50 millimeters, less than 4 millimeters, less than 3 millimeters, less than 2 millimeters, less than 1 millimeter, less than 500 micrometers, or less than 250 micrometers. In some embodiments, the layer between the human skin and the particulate aerogel material comprises an apparel article. The apparel article may be, for example, a glove, a sock, a shoe, a brace, a singlet, or a leotard.

In some embodiments, the solid surface is in direct contact with the particulate aerogel material. In some embodiments, the solid surface is touching the particulate aerogel material with no solid material (e.g., a solid layer) in between the solid surface and the particulate aerogel. For example, in FIG. 10C, the top surface of solid 13 is in direct contact with particulate aerogel material 4.

In some embodiments, the solid surface is in indirect solid contact with the particulate aerogel material. As one example, in FIG. 10F, particulate aerogel material 4 is in indirect solid contact with the top surface of solid 13 because solid layer 22 is in direct contact with both human skin 18 and the top surface of solid 13. In some embodiments in which the particulate aerogel material and the solid surface are in indirect solid contact, the material between the particulate aerogel material and the solid surface is in the form of a layer. For example, in FIG. 10F, layer 22 is present between the top surface of solid 13 and particulate aerogel material 4. In some embodiments the layer has a thickness of less than 5 millimeters, less than 4 millimeters, less than 3 millimeters, less than 2 millimeters, less than 1 millimeter, less than 500 micrometers, or less than 250 micrometers.

In some embodiments, the particulate aerogel material has an average maximum cross-sectional dimension. In some embodiments, the average maximum cross-sectional dimension of the particulate aerogel material is less than or equal to 1 centimeter. In some embodiments, the average maximum cross-sectional dimension of the particulate aerogel material is greater than or equal to 50 nanometers and less than or equal to 1 centimeter. In some embodiments, the average maximum cross-sectional dimension of the particulate aerogel is greater than or equal to 50 nm, greater than or equal to 100 nm, greater than or equal to 250 nm, greater than or equal to 500 nm, greater than or equal to 1 micrometer, greater than or equal to 10 micrometers, greater than or equal to 25 micrometers, greater than or equal to 50 micrometers, greater than or equal to 100 micrometers, greater than or equal to 250 micrometers, greater than or equal to 500 micrometers, greater than or equal to 1 millimeter, or greater than or equal to 1 centimeter. The average maximum cross-sectional dimension is taken as a number average and can be measured using microscopy. In some embodiments, the average maximum cross-sectional dimension of the particulate aerogel material can be determined by placing a representative sample of the particulate aerogel material on a slide or other suitable analysis substrate, imaging the particles (e.g., using image capture hardware and software to capture an image of the particulate aerogel material sample under proper magnification), and then determining the largest cross-sectional dimension of each particle (e.g., using an image processing software to find the maximum cross-sectional dimensions of each discrete particle present in the sample). Suitable magnification devices include an optical microscope or a scanning electron microscope (SEM). The maximum cross-sectional dimensions of all discrete particles are then averaged to determine the average maximum cross-sectional dimension of the sample.

In some embodiments, at least 50 vol % of the particulate aerogel material is made up of particles having a maximum cross-sectional dimension of less than or equal to 1 centimeter. In some embodiments, at least 50 vol % (or at least 60 vol %, at least 70 vol %, at least 80 vol %, at least 90 vol %, or at least 95 vol %) of the particulate aerogel material is made up of particles having a maximum cross-sectional dimension of greater than or equal to 50 nanometers, greater than or equal to 0.1 mm, greater than or equal to 0.7 mm, greater than or equal to 1 mm, and/or less than or equal to 1 centimeter, less than or equal to 3 mm, or less than or equal to 1.2 mm. In some embodiments, at least 50 vol %, at least 60 vol %, at least 70 vol %, at least 80 vol %, at least 90 vol %, or at least 95 vol % of the particulate aerogel material is made up of particles having a maximum cross-sectional dimension of less than or equal to 1 centimeter. In some embodiments, at least 50 vol % of the particulate aerogel material is made up of particles having a maximum cross-sectional dimension of greater than or equal to 50 nanometers and less than or equal to 1 centimeter. In some embodiments, at least 50 vol %, at least 60 vol %, at least 70 vol %, at least 80 vol %, at least 90 vol %, or at least 95 vol % of the particulate aerogel material is made up of particles having a maximum cross-sectional dimension of greater than or equal to 50 nanometers and less than or equal to 1 centimeter. In some embodiments, at least 50 vol %, at least 60 vol %, at least 70 vol %, at least 80 vol %, at least 90 vol %, or at least 95 vol % of the particulate aerogel material is made up of particles having a maximum cross-sectional dimension of greater than or equal to 0.1 mm and less than or equal to 1.2 mm. In certain preferred embodiments, at least 50 vol %, at least 60 vol %, at least 70 vol %, at least 80 vol %, at least 90 vol %, or at least 95 vol % of the particulate aerogel material is made up of particles having a maximum cross-sectional dimension of greater than or equal to 1 mm and less than or equal to 3 mm. In certain preferred embodiments at least 50% of the particulate aerogel material is made up of particles having a maximum cross-sectional dimension of greater than or equal to 0.7 mm and less than or equal to 1.2 mm. In certain preferred embodiments, at least 50 vol %, at least 60 vol %, at least 70 vol %, at least 80 vol %, at least 90 vol %, or at least 95 vol % of the particulate aerogel material is made up of particles having a maximum cross-sectional dimension of greater than or equal to 0.7 mm and less than or equal to 1.2 mm. In certain preferred embodiments, at least 50 vol %, at least 60 vol %, at least 70 vol %, at least 80 vol %, at least 90 vol %, or at least 95 vol % of the particulate aerogel material is made up of particles having a maximum cross-sectional dimension of greater than or equal to 0.1 mm and less than or equal to 4 mm.

In some embodiments, at least 50 vol % (or at least 60 vol %, at least 70 vol %, at least 80 vol %, at least 90 vol %, or at least 95 vol %) of the particulate aerogel material is made up of particles having an ISO 13320-1 cross-sectional dimension of greater than or equal to 50 nanometers, greater than or equal to 0.1 mm, greater than or equal to 0.7 mm, greater than or equal to 1 mm, and/or less than or equal to 1 centimeter, less than or equal to 3 mm, or less than or equal to 1.2 mm. The "ISO 13320-1 cross-sectional dimension," as used herein, refers to the largest cross-sectional dimension of the particulate aerogel when measured by laser diffraction according to the standard ISO 13320-1. In certain preferred embodiments, at least 50 vol %, at least 60 vol %, at least 70 vol %, at least 80 vol %, at least 90 vol %, or at least 95 vol % of the particulate aerogel material is made up of particles having an ISO 13320-1 cross-sectional dimension of greater than or equal to 0.7 mm and less than or equal to 1.2 mm.

In some embodiments, the particulate aerogel material comprises an inorganic oxide aerogel. In some embodiments, at least 50 wt %, at least 60 wt %, at least 70 wt %, at least 80 wt %, at least 90 wt %, at least 95 wt %, at least 99 wt %, at least 99.9 wt %, or at least 99.99 wt % of the particulate aerogel material is made of inorganic oxide aerogel. In some embodiments the inorganic oxide aerogel comprises an oxide of silicon, aluminum, titanium, hafnium, zirconium, chromium, niobium, tantalum, iron, vanadium, neodymium, samarium, holmium, zinc, magnesium, calcium, and/or erbium. In some preferred embodiments, the inorganic oxide aerogel comprises silica aerogel (e.g., in an amount of at least 50 wt %, at least 60 wt %, at least 70 wt %, at least 80 wt %, at least 90 wt %, at least 95 wt %, at least 99 wt %, at least 99.9 wt %, or at least 99.99 wt %). In further preferred embodiments, the inorganic oxide aerogel comprises trimethylsilylated silica aerogel (e.g., in an amount of at least 50 wt %, at least 60 wt %, at least 70 wt %, at least 80 wt %, at least 90 wt %, at least 95 wt %, at least 99 wt %, at least 99.9 wt %, or at least 99.99 wt %).

In some embodiments, the particulate aerogel material may exhibit an internal specific surface area. As used herein, the internal surface area and specific surface area have the same meaning and describe the same phenomenon. As described herein, these values may also be referred to as the BET surface area. The internal specific surface area of a particulate aerogel material may be determined using nitrogen adsorption porosimetry and deriving the surface area value using the Brunauer-Emmett-Teller (BET) model. For example, nitrogen sorption porosimetry may be performed using a Micromeritics Tristar II 3020 surface area and porosity analyzer. Before porosimetry analysis, specimens may be subjected to vacuum of ~100 torr for 24 hours to remove adsorbed water or other solvents from the pores of the specimens. The porosimeter may provide an adsorption isotherm and desorption isotherm, which show the amount of analyte gas adsorbed or desorbed as a function of partial pressure. Specific surface area may be calculated from the adsorption isotherm using the BET method over ranges typically employed in measuring surface area. In some embodiments, the BET surface area of the particulate aerogel material is greater than or equal to 5 $m^2/g$, greater than or equal to 50 $m^2/g$, greater than or equal to 100 $m^2/g$, greater than or equal to 200 $m^2/g$, greater than or equal to 300 $m^2/g$, greater than or equal to 400 $m^2/g$, greater than or equal to 500 $m^2/g$, greater than or equal to 600 $m^2/g$, greater than or equal to 700 $m^2/g$, greater than or equal to 800 $m^2/g$, greater than or equal to 1000 $m^2/g$, greater than or equal to 2000 $m^2/g$, greater than or equal to 3000 $m^2/g$, and/or less than or equal to 1500 $m^2/g$, or less than or equal to 4000 $m^2/g$. In some embodiments, the BET surface area of the particulate aerogel material is greater than or equal to 5 $m^2/g$ and less than or equal to 4000 $m^2/g$. In certain preferred embodiments, the BET surface area of the particulate aerogel material is greater than or equal to 100 $m^2/g$ and less than or equal to 1500 $m^2/g$. Values of the BET surface area of the aerogel outside of these ranges may be possible. In some preferred embodiments, the particulate aerogel material exhibits a BET surface area greater than 200 $m^2/g$. In further preferred embodiments, the particulate aerogel material exhibits a BET surface area greater than 500 $m^2/g$.

The particulate aerogel material may have any of a variety of suitable pore structures. Pore width distribution, pore area distribution, and mean pore size may be calculated from the nitrogen desorption isotherm using the Barrett-Joyner-Halenda (BJH) method over ranges typically reemployed in measuring pore width and pore area distribution. In some embodiments, the particulate aerogel material comprises pores of less than or equal to 100 microns, less than or equal to 10 microns, less than or equal to 1 micron, less than or equal to 500 nm, less than or equal to 250 nm, less than or equal to 100 nm, less than or equal to 50 nm, less than or equal to 25 nm, less than or equal to 20 nm, less than or equal to 15 nm, and/or less than or equal to 10 nm. In some embodiments the aerogel comprises pores of greater than or equal to 10 nm, greater than or equal to 15 nm, greater than or equal to 20 nm, greater than or equal to 25 nm, greater than or equal to 50 nm, greater than or equal to 100 nm, greater than or equal to 250 nm, greater than or equal to 500 nm, greater than or equal to 1 micron, greater than or equal to 10 microns, and or greater than or equal to 100 microns. Average pore width, e.g., mean pore size, (assuming cylindrical pores) may be calculated using pore width=4*(total specific volume)/(specific surface area) where total specific volume and specific surface area may also be calculated using BJH analysis of the desorption isotherm. In some embodiments, the average pore width is less than or equal to 10 nm, less than or equal to 20 nm, less than or equal to 30 nm, less than or equal to 40 nm, less than or equal to 50 nm, less than or equal to 60 nm, less than or equal to 70 nm, less than or equal to 80 nm, less than or equal to 90 nm, less than or equal to 100 nm, less than or equal to 500 nm, less than or equal to 1 µm, less than or equal to 10 µm, less than or equal to 100 µm, or less than or equal to 1 mm. In certain preferred embodiments, the average pore width of the particulate aerogel material is less than or equal to 50 nm. In some preferred embodiments, the average pore width of the particulate aerogel material is less than or equal to 20 nm.

In some embodiments, the pore width distribution of the aerogel may be unimodal (i.e., exhibiting a single maximum). In some embodiments, the pore width distribution maximum is found at less than or equal to 10 nm, less than or equal to 20 nm, less than or equal to 30 nm, less than or equal to 40 nm, less than or equal to 50 nm, less than or equal to 60 nm, less than or equal to 70 nm, less than or equal to 80 nm, less than or equal to 90 nm, less than or equal to 100 nm, less than or equal to 500 nm, less than or equal to 1 µm, less than or equal to 10 µm, less than or equal to 100 µm, or less than or equal to 1 mm. In some embodiments, the aerogel comprises a unimodal pore size distribution.

In some embodiments, the pore width distribution of the aerogel may be bimodal, or at least bimodal. In some embodiments, the aerogel material can have two distinct populations of pores, one with an average pore size less than a certain critical pore width, and one with an average pore size greater than some critical pore width. In some embodiments, the critical pore width is less than or equal to 10 nm, less than or equal to 20 nm, less than or equal to 30 nm, less than or equal to 40 nm, less than or equal to 50 nm, less than or equal to 60 nm, less than or equal to 70 nm, less than or equal to 80 nm, less than or equal to 90 nm, less than or equal to 100 nm, less than or equal to 500 nm, less than or equal to 1 µm, less than or equal to 10 µm, less than or equal to 100 µm, or less than or equal to 1 mm. In some embodiments, the aerogel comprises a bimodal pore size distribution.

In some embodiments, the particulate aerogel material exhibits a BJH pore volume of greater than or equal to 0.05 cm$^3$/g and less than or equal to 5 cm$^3$/g. In some embodiments, the particulate aerogel material exhibits a BJH pore volume of greater than or equal to 0.05 g/cm$^3$, greater than or equal to 1 g/cm$^3$, greater than or equal to 2 g/cm$^3$, greater than or equal to 3 g/cm$^3$, greater than or equal to 4 g/cm$^3$, and/or less than or equal to 5 g/cm$^3$.

In some embodiments, the particulate aerogel material may be present on the skin for a period of time greater than or equal to 1 second, greater than or equal to 1 minute, greater than or equal to 15 minutes, greater than or equal to 30 minutes, greater than or equal to 1 hour, greater than or equal to 4 hours, or greater than or equal to 8 hours. In some embodiments, greater than or equal to 1%, greater than or equal to 5%, greater than or equal to 10%, greater than or equal to 20%, greater than or equal to 30%, greater than or equal to 40%, greater than or equal to 50%, greater than or equal to 60%, greater than or equal to 70%, greater than or equal to 80%, greater than or equal to 90%, or greater than or equal to 95% of the adhered particulate aerogel material may remain on human skin after vigorous exercise. In some embodiments, vigorous exercise may be described as a physical activity lasting more than 15 minutes during which the heart rate increases to at least 120 beats per minute for that period of time during said physical activity. In some embodiments, greater than or equal to 1%, greater than or equal to 5%, greater than or equal to 10%, greater than or equal to 20%, greater than or equal to 30%, greater than or equal to 40%, greater than or equal to 50%, greater than or equal to 60%, greater than or equal to 70%, greater than or equal to 80%, greater than or equal to 90%, or greater than or equal to 95% of the adhered particulate aerogel material may remain on human skin after the particulate aerogel material coated human skin is submerged in water for a period of 5 minutes. In some embodiments, greater than or equal to 1%, greater than or equal to 5%, greater than or equal to 10%, greater than or equal to 20%, greater than or equal to 30%, greater than or equal to 40%, greater than or equal to 50%, greater than or equal to 60%, greater than or equal to 70%, greater than or equal to 80%, greater than or equal to 90%, or greater than or equal to 95% of the adhered particulate aerogel material may remain on human skin after the particulate aerogel material coated human skin contacts a solid surface. Percent of adhered particulate aerogel material remaining on human skin may be determined by visual inspection, optical microscopy, or qualitative touch analysis of the coated human skin.

In some embodiments, the particulate aerogel material is non-toxic to humans. In some embodiments, the particulate aerogel material is non-carcinogenic to humans.

In some embodiments, the particulate aerogel material is non-marking. The particulate aerogel material is considered to be non-marking if the particulate aerogel material does not leave behind a visibly observable permanent deposit of material after contacting a solid surface.

Aerogels are a class of low-density solid materials comprising a porous three-dimensional network of interconnected nanostructures. Aerogels typically exhibit a wide array of desirable materials properties including high specific surface area, low bulk density, low thermal conductivity, and/or low dielectric constant, among others. Aerogels are typically produced through the sol-gel process. Briefly, in such processes, monomers are reacted in a solution to form a dispersion of nanoparticles in liquid called a sol. Alternatively, nanoparticles can be dispersed in a solution to make a sol and in a second step or concurrently with the first step, the particles form a gel. The pore fluid of that gel is then extracted in such a way as to prevent substantial densification leaving behind a highly porous solid (an aerogel). Inorganic oxide aerogels are, generally, natively hydrophilic and express hydroxylated surface functionality that absorbs moisture. Alternatively, inorganic oxide aerogel materials can be made hydrophobic by reacting either the gel in its gel phase, or the dry aerogel, with a reactive hydrophobe. A hydrophobe is generally a reactive chemical agent used to impart hydrophobicity unto a gel or aerogel by changing the composition of surface functional groups that line the backbone of said gel or aerogel. The gel can be reacted with a hydrophobe by soaking in a solution comprising the hydrophobe. The aerogel can be reacted with a hydrophobe by flowing a vapor containing the hydrophobe through the pores of the aerogel. In some embodiments, the hydrophobe may comprise an organosilane. In some preferred embodiments, the hydrophobe comprises hexamethyldisiloxane. In some preferred embodiments, the hydrophobe comprises hexamethyldisilane. In some embodiments, the hydrophobic particulate aerogel material comprises trimethylsilylated silica aerogel.

In some embodiments, particulate aerogel material can be made by first manufacturing a larger aerogel monolith and subsequently breaking the monolith down into particulate matter. Examples of aerogels that can be used in accordance with the present disclosure, and methods for making them, are described in U.S. Pat. No. 10,487,095, issued Nov. 26, 2019, and published as U.S. 2017/0050990 on Feb. 23, 2017; U.S. Pat. No. 10,301,445, issued May 28, 2019, and published as U.S. 2012/0152846 on Jun. 21, 2012; U.S. Pat. No. 10,442,693, issued Oct. 15, 2019, and published as U.S. 2018/0162736 on Jun. 14, 2018; U.S. Patent Application Publication No. 2011/0250428 published on Oct. 13, 2011; U.S. Pat. No. 6,764,667, issued Jul. 20, 2004; and U.S. Pat. No. 10,822,466, issued Nov. 3, 2020, and published as U.S. 2019/0359787 on Nov. 28, 2019; each of which is incorporated herein by reference in its entirety for all purposes.

A "partition coefficient" (P) of a compound is the ratio of concentrations of the compound in a mixture of n-octan-1-ol and water at equilibrium. "Log P" of the compound is the logarithm (Log) of the compound's partition coefficient. The compound's Log P is determined according to the equation below:

$$\text{Log } P = \text{Log } ((\text{Concentration of the compound in the } n\text{-octan-1-ol phase of the mixture})/(\text{Concentration of the compound in the aqueous phase of the mixture})),$$

e.g., when the compound is not ionized in n-octan-1-ol and water. Log P may be determined at about 25° C. and about 1 atm. A higher Log P value may suggest a higher hydrophobicity. In some embodiments, a hydrophobe may have a Log P of greater than or equal to 1, greater than or equal to 1.5, greater than or equal to 2, greater than or equal to 2.5, greater than or equal to 3, greater than or equal to 3.5, or greater than or equal to 4.

In some embodiments, after reacting an inorganic oxide aerogel with a suitable hydrophobe, the Log P of the aerogel is increased. In some embodiments, after reacting an inorganic oxide aerogel with a suitable hydrophobe, the Log P of the reacted aerogel is increased by greater than or equal to 0.5 points, greater than or equal to 1 point, greater than or equal to 1.5 points, greater than or equal to 2 points, greater than or equal to 2.5 points, or greater than or equal to 3 points. In some embodiments, the Log P of the reacted inorganic oxide aerogel is greater than or equal to 1, greater than or equal to 2, greater than or equal to 2.5, greater than or equal to 3, greater than or equal to 3.5, or greater than or equal to 4.

In some embodiments, the aerogels described herein may have a Log P of greater than or equal to 1, greater than or equal to 1.5, greater than or equal to 2, greater than or equal to 2.5, greater than or equal to 3, greater than or equal to 3.5, or greater than or equal to 4.

In some embodiments, the particulate aerogel material may exhibit hydrophobicity. The term hydrophobicity refers to the absence and/or partial absence of attractive force between a material and a mass of water. In some embodiments, the hydrophobicity of a bulk material refers to this behavior as it applies to a surface. In certain embodiments, the apparent hydrophobicity of a textured surface can be higher than the chemical hydrophobicity of the bulk material.

Hydrophobicity of the particulate aerogel material can be expressed in terms of the liquid water uptake. The term liquid water uptake refers to the ability of a material or composition to absorb, adsorb, or otherwise retain water due to contact with water in the liquid state. Liquid water uptake can be expressed one of several ways, for example, as a fraction or percent of the open pore volume or envelope volume of the particulate aerogel material, or as a fraction or percent relative to the mass of the unwetted particulate aerogel material. The liquid water uptake reported is understood to be a measurement undertaken under specific conditions. A particulate aerogel material that has superior or improved liquid water uptake relative to a different particulate aerogel material is understood to have a lower uptake of liquid water.

In some embodiments, the particulate aerogel material has a liquid water uptake of less than 100 wt %, less than 80 wt %, less than 70 wt %, less than 60 wt %, less than 50 wt %, less than 40 wt %, less than 30 wt %, less than 20 wt %, less than 10 wt %, less than 5 wt %, less than 4 wt %, less than 3 wt %, less than 2 wt %, less than 1 wt %, or less than 0.1 wt % relative to the weight of the particulate aerogel material before contact with liquid water when measured according to standard ASTM C1763.

In some embodiments, the particulate aerogel material has a liquid water uptake of less than 100 wt %, less than 80 wt %, less than 70 wt %, less than 60 wt %, less than 50 wt %, less than 40 wt %, less than 30 wt %, less than 20 wt %, less than 10 wt %, less than 5 wt %, less than 4 wt %, less than 3 wt %, less than 2 wt %, less than 1 wt %, or less than 0.1 wt % relative to the weight of the particulate aerogel material before contact with liquid water when measured according to standard EN 1609.

In some embodiments, when the particulate aerogel material is submerged under water at 25° C. for 24 h, the particulate aerogel material uptakes a mass of water within its outer boundaries of less than 30% of the dry mass of the particulate aerogel material prior to submerging in the water.

Hydrophobicity of the particulate aerogel material can be expressed in terms of the water contact angle. The term water contact angle refers to the equilibrium contact angle of a drop of water in contact with a surface made of the particulate aerogel material. The contact angle can be determined as follows: A polycarbonate annulus with a 2 cm outer diameter and a 1 cm inner diameter, that is 2 cm tall and sealed on one end by a flat piece of polycarbonate forming a 2 cm deep well is prepared. Particulate aerogel material is added to the top of the well. The polycarbonate cylinder is then tapped 10 times to allow the particulate aerogel material to settle. More particulate aerogel material is added, and this process is repeated until the level of particulate in the polycarbonate cylinder is level with or above the top of the well. A metal laboratory spatula is then dragged across the top of the well to scrape away excess material and help ensure the flatness of the testing area. A droplet of deionized water is them deposited via Pasteur pipette atop the center of the particulate aerogel material. A photo of the droplet of water is then captured from the side of the droplet. The image of the droplet is then processed using an image processing software to measure the contact angle between the droplet and the top surface of the particulate in the well, where the contact angle is measured through the bulk of the droplet. In some embodiments, the particles are milled or crushed prior to testing such that the average maximum cross-sectional dimension of the aerogel particles is greater than or equal to 2 micrometers and less than or equal to 40 micrometers. Without wishing to be bound by any particular theory, it is believed that, in some embodiments, a smaller particle size allows for tighter packing of the particulate aerogel material to reduce textural surface effects on the contact angle measurement. Without wishing to be bound by any particular theory, it is believed that a particulate aerogel that exhibits a higher water contact angle relative to a second particulate aerogel material may have a superior or improved hydrophobicity relative to that second particulate aerogel material. In some embodiments, when the particulate aerogel material is tested according to this method, the water contact angle may be greater than 90°, greater than 100°, greater than 110°, greater than 120°, greater than 130°, greater than 140°, greater than 150°, greater than 160°, greater than 170°, or between 170° and 180° in ambient air at least one temperature and pressure. In some embodiments, when the particulate aerogel material is tested according to this method, the water contact angle may be greater than 90°, greater than 100°, greater than 110°, greater than 120°, greater than 130°, greater than 140°, greater than 150°, greater than 160°, greater than 170°, or between 170° and 180° in ambient air at 1 atm pressure and 25° C. In some preferred embodiments, the particulate aerogel material exhibits a contact angle with water, in an ambient air environment at 1 atm and 25° C., of greater than 90° when measured according to the test described herein.

Hydrophobicity of the particulate aerogel material can be expressed in terms of the water vapor uptake. The term water vapor uptake refers to the ability for a material or composition to absorb, adsorb, or otherwise retain water due to contact with water in the vapor state. Water vapor uptake can be expressed as a fraction or percent of water retained relative to the mass of the particulate aerogel material before exposure to water vapor. The water vapor uptake reported is understood to be a measurement undertaken under specific conditions. A particulate aerogel material which has superior or improved water vapor uptake relative to a different particulate aerogel material is understood to have a lower sorption or retention of water vapor. In some embodiments, the water uptake may be less than 100 wt %, less than 80 wt %, less than 70 wt %, less than 60 wt %, less than 50 wt %, less than 40 wt %, less than 30 wt %, less than 20 wt %, less than 10 wt %, less than 5 wt %, less than 4 wt %, less than 3 wt %, less than 2 wt %, less than 1 wt %, or less than 0.1 wt % relative to the weight of the particulate aerogel material before exposure to water vapor, when measured according to standard ASTM C1104.

Hydrophobicity of the particulate aerogel material can be expressed in terms of retained internal surface area after submersion in water. After submersion in deionized water, the particulate aerogel material is allowed to dry out completely, and then nitrogen sorption porosimetry is performed as outlined herein to measure the remaining internal surface area of the material. In some embodiments, the particulate aerogel material retains greater than 5%, greater than 10%, greater than 15%, greater than 20%, greater than 25%, greater than 30%, greater than 40%, greater than 50%, greater than 60%, greater than 70%, greater than 80%, greater than 90%, or greater than 95% of the internal surface area of the same particulate aerogel material prior to submersion in water.

In some embodiments the particulate aerogel material exhibits an optical transmission of greater than or equal to 5% at 635 nm.

In some embodiments, the particulate aerogel material may exhibit a relatively high light transmission. In some embodiments, the particulate aerogel material exhibits a light transmission of greater than or equal to 5%, greater than or equal to 10%, greater than or equal to 20%, greater than or equal to 30%, greater than or equal to 40%, greater than or equal to 50%, greater than or equal to 60%, greater than or equal to 70%, greater than or equal to 80%, greater than or equal to 90%, or greater than or equal to 95% when tested according to ASTM E424. In some preferred embodiments, the particulate aerogel material exhibits a light transmission of greater than or equal to 89% per cm when tested according to ASTM E424.

In some embodiments, the particulate aerogel material readily absorbs natural oils from human skin. In some embodiments, the particulate aerogel material exhibits a mineral oil uptake that can serve as a proxy test for gauging the particulate aerogel material's ability to absorb natural oil excreted from human skin. The term mineral oil uptake refers to the ability of a material or composition to absorb, adsorb, or otherwise retain mineral oil due to contact with mineral oil. Mineral oil uptake can be expressed as a fraction or percent relative to the mass of the unwetted particulate aerogel material. The mineral oil uptake described herein is measured using CAS number 8012-95-1 mineral oil from Sigma Aldrich. A particulate aerogel material that has superior or improved mineral oil uptake relative to a different particulate aerogel material is understood to have a higher uptake of mineral oil. In some embodiments, the mineral oil uptake may be greater than or equal to 0.1 wt %, greater than or equal to 1 wt %, greater than or equal to 2 wt %, greater than or equal to 3 wt %, greater than or equal to 4 wt %, greater than or equal to 5 wt %, greater than or equal to 10 wt %, greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 100 wt %, greater than or equal to 200 wt %, greater than or equal to 300 wt %, greater than or equal to 500 wt %, or greater than or equal to 1000 wt % relative to the weight of the particulate aerogel material before submersion in mineral oil.

In some embodiments, the particulate aerogel material is submerged under mineral oil for 24 hours at 25° C., the particulate aerogel material uptakes a mass of mineral oil within the outer boundaries of the particulate of greater than or equal to 20% of the dry mass of the particulate aerogel material just prior to submerging in mineral oil.

In some embodiments, the particulate aerogel material will fracture when subjected to a pressure of less than 1 $N/cm^2$. In some embodiments, the particulate aerogel material will fracture when subjected to a pressure of less than or equal to 10 kPa, less than or equal to 20 kPa, less than or equal to 50 kPa, less than or equal to 100 kPa, or less than or equal to 200 kPa. The pressure at which the particulate aerogel material will fracture can be measured according to the following. An optically transparent polycarbonate annulus with a 2 cm outer diameter and a 1 cm inner diameter, that is 2 cm tall and sealed on one end by a flat piece of polycarbonate forming a 2 cm deep well, said well having a level marking on the side of its outer surface corresponding to a well depth of 1 cm, is prepared. Particulate aerogel material is added to the level line within the well. The polycarbonate well is then tapped 10 times to allow the particulate aerogel material to settle. More particulate aerogel material is added, and this process is repeated until the level of particulate in the polycarbonate well is exactly at the 1 cm depth level mark. The polycarbonate annulus is then centered between the compressive platens on a universal testing machine (e.g., an Instron 3366). A 0.9 cm diameter polycarbonate rod that is 2 cm tall is gently placed on top of the aerogel in the well of the polycarbonate annulus. The compressive platens are then compressed at a rate of 1 mm/s and the force is recorded as a function of displacement, until a force of 0.64N is reached, corresponding to a pressure exerted by the cylinder of 200 kPa, or the 2 cm rod can no longer be depressed. The compressive platens are then returned to their starting positions, to remove the external load on the volume of aerogel. The material is stated to be crushable if a stress of less than or equal to 200 kPa results in the breaking of at least one particle in the well into two or more pieces as determined through visual observation before and after the test. In some embodiments, permanent compaction of the volume of the particulate aerogel material in the well results from the test described herein, such that there is a permanent compressive axial deflection of the volume of particles in an amount greater than 5% after a stress of 200 kPa has been applied. In some embodiments, the particulate aerogel material will fracture when subjected to a pressure of less than 1 N/cm$^2$.

Without wishing to be bound by any particular theory, in some embodiments a crushable particulate aerogel material may be advantageous for enhancing grip (e.g., increasing friction between human skin and a solid surface) as the aerogel particulate may be more easily distributed and/or retained on the human skin and/or solid surface. In some embodiments, the particulate aerogel material is able to be fractured with minimal effort by a human woman with average strength. In some embodiments, the particulate aerogel material is able to be fractured by a human woman with less than average strength. In some embodiments, the particulate aerogel material is able to be fractured by a human male with average strength. In some embodiments, the particulate aerogel material is able to be fractured by a human male with less than average strength.

In some embodiments, friction between the human skin and the solid surface, when the particulate aerogel is present between the human skin and the solid surface, is higher than it would be under otherwise identical conditions without the particulate aerogel.

In some embodiments, particulate aerogel material is used to increase friction between human skin and a solid surface (and/or between a surface of a material with which the human skin is in contact and a solid surface), where the solid surface is part of a grippable object. In some embodiments, particulate aerogel material is used to increase friction between human skin and a solid surface (and/or between a surface of a material with which the human skin is in contact and a solid surface), where the solid surface is part of a handle. In some embodiments, particulate aerogel material is used to increase friction between human skin and a solid surface (and/or between a surface of a material with which the human skin is in contact and a solid surface), where the solid surface is part of a grip. The grip and/or the handle may, in some embodiments, comprise a contour that at least partially conforms to a human hand. In some embodiments, the solid surface (e.g., of a grip and/or a handle) is made of leather. In some embodiments, the solid surface (e.g., of a grip and/or a handle) is made of wood. In some embodiments, the solid surface (e.g., of a grip and/or a handle) is made of polymer (e.g., synthetic leather, flexible polyurethane, or other polymers). In some embodiments, the solid surface (e.g., of a grip and/or a handle) is made of metal. In some embodiments, the solid surface (e.g., of a grip and/or a handle) is made of foam. In some embodiments, the solid surface (e.g., of a grip and/or a handle) is made of ivory. In some embodiments, the solid surface (e.g., of a grip and/or a handle) is made of fabric. In some embodiments, the solid surface (e.g., of a grip and/or a handle) is made of ceramic. In some embodiments, the solid surface (e.g., of a grip and/or a handle) is made of composite. In some embodiments, the solid surface (e.g., of a grip and/or a handle) is made of geologic material.

In some embodiments, particulate aerogel material is used to increase friction between human skin and a solid surface (and/or between a surface of a material with which the human skin is in contact and a solid surface), where the solid surface is part of a musical instrument (e.g., a handle and/or a grip of a music instrument). In some embodiments the musical instrument is a guitar. In some embodiments, the musical instrument is a piano. In some embodiments, the musical instrument is a violin. In some embodiments, the musical instrument is a viola. In some embodiments, the musical instrument is a cello. In some embodiments, the musical instrument is a bass. In some embodiments, the musical instrument is an organ. In some embodiments, the musical instrument is a keytar. In some embodiments, the musical instrument is an accordion. In some embodiments, the musical instrument is a keyboard. In some embodiments, the musical instrument is a concertina. In some embodiments, the musical instrument is a ukulele. In some embodiments, the musical instrument is a melodica. In some embodiments, the musical instrument is a lute. In some embodiments, the musical instrument is a harmonica. In some embodiments, the musical instrument is a recorder. In some embodiments, the musical instrument is a bagpipe. In some embodiments, the musical instrument is a tuba. In some embodiments, the musical instrument is a trumpet. In some embodiments, the musical instrument is a French horn. In some embodiments, the musical instrument is a trombone. In some embodiments, the musical instrument is a saxophone. In some embodiments, the musical instrument is a clarinet. In some embodiments, the musical instrument is an oboe. In some embodiments, the musical instrument is a flute. In some embodiments, the musical instrument is a sousaphone. In some embodiments, the musical instrument is a flugelhorn. In some embodiments, the musical instrument is a cornet. In some embodiments, the musical instrument is a euphonium. In some embodiments, the musical instrument is the bells.

In some embodiments, particulate aerogel material is used to increase friction between human skin and a solid surface (and/or between a surface of a material with which the human skin is in contact and a solid surface), where the solid surface is part of a musical instrument accessory (e.g., a handle and/or grip of a musical instrument accessory). In some embodiments, the musical instrument accessory is a guitar pick. In some embodiments, the musical instrument accessory is a drumstick. In some embodiments, the musical instrument accessory is a violin bow. In some embodiments, the musical instrument accessory is a viola bow. In some embodiments, the musical instrument accessory is a cello bow. In some embodiments, the musical instrument accessory is a bass bow. In some embodiments, the musical instrument accessory is a xylophone mallet. In some embodiments, the musical instrument accessory is a conductor's wand.

In some embodiments, particulate aerogel material is used to increase friction between human skin and a solid surface (and/or between a surface of a material with which the human skin is in contact and a solid surface), where the solid surface is part of a piece of sports equipment (e.g., a handle and/or a grip of a piece of sports equipment). In some embodiments, the sports equipment is a baseball bat. In some embodiments, the sports equipment is a baseball glove. In some embodiments, the sports equipment is a tennis racket. In some embodiments, the sports equipment is badminton racket. In some embodiments, the sports equipment is a racket. In some embodiments, the sports equipment is a golf club. In some embodiments, the sports equipment is a dart. In some embodiments, the sports equipment is an arrow. In some embodiments, the sports equipment is a bow. In some embodiments, the sports equipment is flagpole. In some embodiments, the sports equipment is a paddle. In some embodiments, the sports equipment is a pole. In some embodiments, the sports equipment is a mast. In some embodiments, the sports equipment is a frisbee. In some embodiments, the sports equipment is a hammer. In some embodiments, the sports equipment is an oar. In some embodiments, the sports equipment is a whip. In some embodiments, the sports equipment is a lasso. In some embodiments, the sports equipment is a sword. In some embodiments, the sports equipment is a javelin. In some embodiments, the sports equipment is a shotput. In some embodiments, the sports equipment is a discus. In some embodiments, the sports equipment is a foil. In some embodiments, the sports equipment is a sabre. In some embodiments, the sports equipment is an epee. In some embodiments, the sports equipment is a lacrosse stick. In some embodiments, the sports equipment is a hockey stick. In some embodiments, the sports equipment is a field hockey stick. In some embodiments, the sports equipment is a parasail. In some embodiments, the sports equipment is a wakeboard. In some embodiments, the sports equipment is a paddleboard. In some embodiments, the sports equipment is a squash racket. In some embodiments, the sports equipment is a jai alai cesta. In some embodiments, the sports equipment is a curling broom. In some embodiments, the sports equipment is a curling stone. In some embodiments, the sports equipment is a hurling stick. In some embodiments, the sports equipment is a cricket bat. In some embodiments, the sports equipment is a ski pole. In some embodiments, the sports equipment is a pompom. In some embodiments, the sports equipment is a boxing glove. In some embodiments, the sports equipment is a horse rein. In some embodiments, the sports equipment is a fishing pole. In some embodiments, the sports equipment is a fishing net. In some embodiments, the sports equipment is a snowmobile. In some embodiments, the sports equipment is a pool cue. In some embodiments, the sports equipment is a sled. In some embodiments, the sports equipment is an air hockey puck. In some embodiments, the sports equipment is a table tennis paddle. In some embodiments, the sports equipment is a skateboard. In some embodiments, the sports equipment is a polo mallet. In some embodiments, the sports equipment is a gi. In some embodiments, the sports equipment is a wetsuit. In some embodiments, the sports equipment is a softball bat.

In some embodiments, particulate aerogel material is used to increase friction between human skin and a solid surface (and/or between a surface of a material with which the human skin is in contact and a solid surface), where the solid surface is part of a ball. In some embodiments, the ball is a baseball. In some embodiments, the ball is a basketball. In some embodiments, the ball is a football. In some embodiments, the ball is a rugby ball. In some embodiments, the ball is a softball. In some embodiments, the ball is a racquetball. In some embodiments, the ball is a dodgeball. In some embodiments, the ball is a volleyball. In some embodiments, the ball is a tetherball. In some embodiments, the ball is a kickball. In some embodiments, the ball is a whiffle ball. In some embodiments, the ball is a lacrosse ball. In some embodiments, the ball is a squash ball. In some embodiments, the ball is a handball. In some embodiments, the ball is a spaldeen. In some embodiments, the ball is a juggling ball. In some embodiments, the ball is a cricket ball. In some embodiments, the ball is a bowling ball. In some embodiments, the ball is a golf ball. In some embodiments, the ball is a water polo ball. In some embodiments, the ball is a pickle ball.

In some embodiments, particulate aerogel material is used to increase friction between human skin and a solid surface (and/or between a surface of a material with which the human skin is in contact and a solid surface), where the solid surface is part of a handlebar. In some embodiments, the handlebar is part of a bicycle. In some embodiments, the handlebar is part of a motorcycle. In some embodiments, the handlebar is part of an electric bicycle. In some embodiments, the handlebar is part of a razor scooter. In some embodiments, the handlebar is part of an electric scooter. In some embodiments, the handlebar is part of a dirt bike. In some embodiments, the handlebar is part of a motocross bike. In some embodiments, the handlebar is part of a mountain bike. In some embodiments, the handlebar is part of a snowmobile. In some embodiments, the handlebar is part of a jet ski. In some embodiments, the handlebar is part of a glider.

In some embodiments, particulate aerogel material is used to increase friction between human skin and a solid surface (and/or between a surface of a material with which the human skin is in contact and a solid surface), where the solid surface is part of a steering wheel. In some embodiments, the steering wheel is part of a car. In some embodiments, the steering wheel is part of a truck. In some embodiments, the steering wheel is part of a four-wheeler. In some embodiments, the steering wheel is part of a monster truck. In some embodiments, the steering wheel is part of a boat.

In some embodiments, particulate aerogel material is used to increase friction between human skin and a solid surface (and/or between a surface of a material with which the human skin is in contact and a solid surface), where the solid surface is part of a rock. In some embodiments, the rock is a synthetic rock. In some embodiments, the rock is a natural rock. In some embodiments, the rock is or is part of a mountain.

In some embodiments, particulate aerogel material is used to increase friction between human skin and a solid surface (and/or between a surface of a material with which the human skin is in contact and a solid surface), where the solid surface is part of a mat. In some embodiments, the mat is a wrestling mat. In some embodiments, the mat is a gymnastics mat.

In some embodiments, particulate aerogel material is used to increase friction between human skin and a solid surface (and/or between a surface of a material with which the human skin is in contact and a solid surface), where the solid surface is part of a tool (e.g., part of a grip and/or a handle of a tool). In some embodiments, the tool is a power drill. In some embodiments, the tool is a screwdriver. In some embodiments, the tool is a wrench. In some embodiments, the tool is a hammer. In some embodiments, the tool is a crowbar. In some embodiments, the tool is a saw. In some embodiments, the tool is a shovel. In some embodiments, the tool is a pitchfork. In some embodiments, the tool is a hoe. In some embodiments, the tool is a spade. In some embodiments, the tool is a pick.

In some embodiments, particulate aerogel material is used to increase friction between human skin and a solid surface (and/or between a surface of a material with which the human skin is in contact and a solid surface), where the solid surface is part of a video game controller (e.g., part of a grip and/or a handle of a video game controller). In some embodiments, the video game controller is a mouse. In some embodiments, the video game controller is a keyboard. In some embodiments, the video game controller is a joystick. In some embodiments, the video game controller is a video game console controller. In some embodiments, the video game controller is a video game console.

In some embodiments, particulate aerogel material is used to increase friction between human skin and a solid surface (and/or between a surface of a material with which the human skin is in contact and a solid surface), where the solid surface is part of a firearm (e.g., part of a grip and/or a handle of a firearm). In some embodiments, the firearm is a handgun. In some embodiments, the firearm is a rifle. In some embodiments, the firearm is a machine gun. In some embodiments, the firearm is an automatic weapon. In some embodiments, the firearm is a semi-automatic weapon. In some embodiments, the firearm is a revolver. In some embodiments, the firearm is a shotgun.

In some embodiments, particulate aerogel material is used to increase friction between human skin and a solid surface (and/or between a surface of a material with which the human skin is in contact and a solid surface), where the solid surface is part of a piece of weightlifting equipment (e.g., part of a grip and/or a handle of weightlifting equipment). In some embodiments, the piece of weightlifting equipment is a barbell. In some embodiments, the piece of weightlifting equipment is a dumbbell. In some embodiments, the piece of weightlifting equipment is a kettle bell. In some embodiments, the piece of weightlifting equipment is a pull up bar. In some embodiments, the piece of weightlifting equipment is an atlas stone. In some embodiments, the piece of weightlifting equipment is a sandbag. In some embodiments, the piece of weightlifting equipment is a yoke. In some embodiments, the piece of weightlifting equipment is a farmers walk handle. In some embodiments, the piece of weightlifting equipment is a carpet sled. In some embodiments, the piece of weightlifting equipment is a log bar. In some embodiments, the piece of weightlifting equipment is an ez-curl bar.

In some embodiments, particulate aerogel material is used to increase friction between human skin and a solid surface (and/or between a surface of a material with which the human skin is in contact and a solid surface), where the solid surface is part of a piece of gymnastics equipment (e.g., part of a grip and/or a handle of a piece of gymnastics equipment). In some embodiments, the piece of gymnastics equipment is uneven bars. In some embodiments, the piece of gymnastics equipment is parallel bars. In some embodiments, the piece of gymnastics equipment is rings. In some embodiments, the piece of gymnastics equipment is a balance beam. In some embodiments, the piece of gymnastics equipment is a trapeze. In some embodiments, the piece of gymnastics equipment is a baton. In some embodiments, the piece of gymnastics equipment is a trampoline. In some embodiments, the piece of gymnastics equipment is a vault. In some embodiments, the piece of gymnastics equipment is a pommel horse. In some embodiments, the piece of gymnastics equipment is a horizontal bar. In some embodiments, the piece of gymnastics equipment is a floor mat.

In some embodiments, particulate aerogel material is used to increase friction between human skin and a solid surface (and/or between a surface of a material with which the human skin is in contact and a solid surface), where the solid surface is part of a doorknob. In some embodiments, particulate aerogel material is used to increase friction between human skin and a solid surface (and/or between a surface of a material with which the human skin is in contact and a solid surface), where the solid surface is part of a helmet. In some embodiments, particulate aerogel material is used to increase friction between human skin and a solid surface (and/or between a surface of a material with which the human skin is in contact and a solid surface), where the solid surface is part of other human skin. In some embodiments, particulate aerogel material is used to increase friction between human skin and a solid surface (and/or between a surface of a material with which the human skin is in contact and a solid surface), where the solid surface is part of a helicopter. In some embodiments, particulate aerogel material is used to increase friction between human skin and a solid surface (and/or between a surface of a material with which the human skin is in contact and a solid surface), where the solid surface is part of a rope. In some embodiments, particulate aerogel material is used to increase friction between human skin and a solid surface (and/or between a surface of a material with which the human skin is in contact and a solid surface), where the solid surface is part of a ladder. In some embodiments, particulate aerogel material is used to increase friction between human skin and a solid surface (and/or between a surface of a material with which the human skin is in contact and a solid surface), where the solid surface is part of a camera. In some embodiments, particulate aerogel material is used to increase friction between human skin and a solid surface (and/or between a surface of a material with which the human skin is in contact and a solid surface), where the solid surface is part of a piece of wood. In some embodiments, particulate aerogel material is used to increase friction between human skin and a solid surface (and/or between a surface of a material with which the human skin is in contact and a solid surface), where the solid surface is part of a piece of metal. In some embodiments, particulate aerogel material is used to increase friction between human skin and a solid surface (and/or between a surface of a material with which the human skin is in contact and a solid surface), where the solid surface is part of a torch. In some embodiments, particulate aerogel material is used to increase friction between human skin and a solid surface (and/or between a surface of a material with which the human skin is in contact and a solid surface), where the solid surface is part of a piece of plastic. In some embodiments, particulate aerogel material is used to increase friction between human skin and a solid surface (and/or between a surface of a material with which the human skin is in contact and a solid surface), where the solid surface is part of a piece of ceramic. In some embodiments, particulate aerogel material is used to increase friction between human skin and a solid surface (and/or between a surface of a material with which the human skin is in contact and a solid surface), where the solid surface is part of a composite. In some embodiments, particulate aerogel material is used to increase friction between human skin and a solid surface (and/or between a surface of a material with which the human skin is in contact and a solid surface), where the solid surface is part of a shoe. In some embodiments, particulate aerogel material is used to increase friction between human skin and a solid surface (and/or between a surface of a material with which the human skin is in contact and a solid surface), where the solid surface is part of a glove (e.g., the interior of a glove). In some embodiments, particulate aerogel material is used to increase friction between human skin and a solid surface (and/or between a surface of a material with which the human skin is in contact and a solid surface), where the solid surface is part of a sock. In some embodiments, particulate aerogel material is used to increase friction between human skin and a solid surface (and/or between a surface of a material with which the human skin is in contact and a solid surface), where the solid surface is part of a chain. In some embodiments, particulate aerogel material is used to increase friction between human skin and a solid surface (and/or between a surface of a material with which the human skin is in contact and a solid surface), where the solid surface is part of a microphone. In some embodiments, particulate aerogel material is used to increase friction between human skin and a solid surface (and/or between a surface of a material with which the human skin is in contact and a solid surface), where the solid surface is part of a cardboard box. In some embodiments, particulate aerogel material is used to increase friction between human skin and a solid surface (and/or between a surface of a material with which the human skin is in contact and a solid surface), where the solid surface is part of a Styrofoam box. In some embodiments, particulate aerogel material is used to increase friction between human skin and a solid surface (and/or between a surface of a material with which the human skin is in contact and a solid surface), where the solid surface is part of a cooler. In some embodiments, particulate aerogel material is used to increase friction between human skin and a solid surface (and/or between a surface of a material with which the human skin is in contact and a solid surface), where the solid surface is part of an umbrella. In some embodiments, particulate aerogel material is used to increase friction between human skin and a solid surface (and/or between a surface of a material with which the human skin is in contact and a solid surface), where the solid surface is part of a smartphone. In some embodiments, particulate aerogel material is used to increase friction between human skin and a solid surface (and/or between a surface of a material with which the human skin is in contact and a solid surface), where the solid surface is part of a computer. In some embodiments, particulate aerogel material is used to increase friction between human skin and a solid surface (and/or between a surface of a material with which the human skin is in contact and a solid surface), where the solid surface is part of a tablet. In some embodiments, particulate aerogel material is used to increase friction between human skin and a solid surface (and/or between a surface of a material with which the human skin is in contact and a solid surface), where the solid surface is part of a piece of furniture. In some embodiments, particulate aerogel material is used to increase friction between human skin and a solid surface (and/or between a surface of a material with which the human skin is in contact and a solid surface), where the solid surface is part of a door. In some embodiments, particulate aerogel material is used to increase friction between human skin and a solid surface (and/or between a surface of a material with which the human skin is in contact and a solid surface), where the solid surface is part of a video camera. In some embodiments, particulate aerogel material is used to increase friction between human skin and a solid surface (and/or between a surface of a material with which the human skin is in contact and a solid surface), where the solid surface is part of a boom mic. In some embodiments, particulate aerogel material is used to increase friction between human skin and a solid surface (and/or between a surface of a material with which the human skin is in contact and a solid surface), where the solid surface is part of a switch. In some embodiments, particulate aerogel material is used to increase friction between human skin and a solid surface (and/or between a surface of a material with which the human skin is in contact and a solid surface), where the solid surface is part of a parachute. In some embodiments, particulate aerogel material is used to increase friction between human skin and a solid surface (and/or between a surface of a material with which the human skin is in contact and a solid surface), where the solid surface is part of a hot air balloon. In some embodiments, particulate aerogel material is used to increase friction between human skin and a solid surface (and/or between a surface of a material with which the human skin is in contact and a solid surface), where the solid surface is part of a katana. In some embodiments, particulate aerogel material is used to increase friction between human skin and a solid surface (and/or between a surface of a material with which the human skin is in contact and a solid surface), where the solid surface is part of a nunchaku. In some embodiments, particulate aerogel material is used to increase friction between human skin and a solid surface (and/or between a surface of a material with which the human skin is in contact and a solid surface), where the solid surface is part of a sai. In some embodiments, particulate aerogel material is used to increase friction between human skin and a solid surface (and/or between a surface of a material with which the human skin is in contact and a solid surface), where the solid surface is part of a shuriken. In some embodiments, particulate aerogel material is used to increase friction between human skin and a solid surface (and/or between a surface of a material with which the human skin is in contact and a solid surface), where the solid surface is part of a taser. In some embodiments, particulate aerogel material is used to increase friction between human skin and a solid surface (and/or between a surface of a material with which the human skin is in contact and a solid surface), where the solid surface is part of a spray can. In some embodiments, particulate aerogel material is used to increase friction between human skin and a solid surface (and/or between a surface of a material with which the human skin is in contact and a solid surface), where the solid surface is part of a megaphone. In some embodiments, particulate aerogel material is used to increase friction between human skin and a solid surface (and/or between a surface of a material with which the human skin is in contact and a solid surface), where the solid surface is part of a face. In some embodiments, particulate aerogel material is used to increase friction between human skin and a solid surface (and/or between a surface of a material with which the human skin is in contact and a solid surface), where the solid surface is part of a wall. In some embodiments, particulate aerogel material is used to increase friction between human skin and a solid surface (and/or between a surface of a material with which the human skin is in contact and a solid surface), where the solid surface is part of a window. In some embodiments, particulate aerogel material is used to increase friction between human skin and a solid surface (and/or between a surface of a material with which the human skin is in contact and a solid surface), where the solid surface is part of a boot. In some embodiments, particulate aerogel material is used to increase friction between human skin and a solid surface (and/or between a surface of a material with which the human skin is in contact and a solid surface), where the solid surface is part of crutches. In some embodiments, particulate aerogel material is used to increase friction between human skin and a solid surface (and/or between a surface of a material with which the human skin is in contact and a solid surface), where the solid surface is part of a walker. In some embodiments, particulate aerogel material is used to increase friction between human skin and a solid surface (and/or between a surface of a material with which the human skin is in contact and a solid surface), where the solid surface is part of a cane. In some embodiments, particulate aerogel material is used to increase friction between human skin and a solid surface (and/or between a surface of a material with which the human skin is in contact and a solid surface), where the solid surface is part of a backpack. In some embodiments, particulate aerogel material is used to increase friction between human skin and a solid surface (and/or between a surface of a material with which the human skin is in contact and a solid surface), where the solid surface is part of a shopping bag. In some embodiments, particulate aerogel material is used to increase friction between human skin and a solid surface (and/or between a surface of a material with which the human skin is in contact and a solid surface), where the solid surface is part of a disk. In some embodiments, particulate aerogel material is used to increase friction between human skin and a solid surface (and/or between a surface of a material with which the human skin is in contact and a solid surface), where the solid surface is part of a tray. In some embodiments, particulate aerogel material is used to increase friction between human skin and a solid surface (and/or between a surface of a material with which the human skin is in contact and a solid surface), where the solid surface is part of another human. In some embodiments, particulate aerogel material is used to increase friction between human skin and a solid surface (and/or between a surface of a material with which the human skin is in contact and a solid surface), where the solid surface is part of an animal. In some embodiments, particulate aerogel material is used to increase friction between human skin and a solid surface (and/or between a surface of a material with which the human skin is in contact and a solid surface), where the solid surface is part of a wheelchair. In some embodiments, particulate aerogel material is used to increase friction between human skin and a solid surface (and/or between a surface of a material with which the human skin is in contact and a solid surface), where the solid surface is part of a knob. In some embodiments, particulate aerogel material is used to increase friction between human skin and a solid surface (and/or between a surface of a material with which the human skin is in contact and a solid surface), where the solid surface is part of a button. In some embodiments, particulate aerogel material is used to increase friction between human skin and a solid surface (and/or between a surface of a material with which the human skin is in contact and a solid surface), where the solid surface is part of a directional pad. In some embodiments, particulate aerogel material is used to increase friction between human skin and a solid surface (and/or between a surface of a material with which the human skin is in contact and a solid surface), where the solid surface is part of a floor. In some embodiments, particulate aerogel material is used to increase friction between human skin and a solid surface (and/or between a surface of a material with which the human skin is in contact and a solid surface), where the solid surface is part of the ground or floor.

In some embodiments an article comprises a flexible container and a particulate aerogel material within the container. In some embodiments, the flexible container comprises fabric, paper, plastic, or rubber, or a combination of the foregoing. In certain embodiments, at least a portion of a boundary of the container is porous and permits transport of the particulate aerogel through the porous boundary upon application of force to the flexible container. In some embodiments, applying force to the flexible container may comprise squeezing the container. In some embodiments, applying force to the flexible container may comprise rolling the container. In some embodiments, applying force to the flexible container may comprise stepping on the container. In some embodiments, applying force to the flexible container may comprise crushing the container.

In some embodiments, applying force to the flexible container fractures the particulate aerogel material inside the container and the new, smaller, particulate is able to be transported through at least a portion of one boundary of the container.

In some embodiments, the flexible container has a volume of less than or equal to 5000 $cm^3$, less than or equal to 2000 $cm^3$, less than or equal to 1000 $cm^3$, or less than or equal to 500 $cm^3$. In some embodiments, the container has a volume of at least 0.1 $cm^3$, at least 0.5 $cm^3$, or at least 1 $cm^3$. In some embodiments, the flexible container has a volume such that the container can be held comfortably in the hand of an American man of average size. In some embodiments, the ability for the container to fit comfortably in the palm of the average sized American male, enables ease of use and transport of the container.

In some embodiments, the flexible container has a volume such that the container occupies a footprint of at least 100 $cm^2$ when a pressure of 100 $N/cm^2$ is applied to the container. In some embodiments, the flexible container has a volume such that the container can be stepped on and will cover the surface area of the average foot of the American male. In some embodiments, the size of the container covering the surface area of the foot of the average American male allows for convenient application of the particulate aerogel material to the foot after stepping on the container.

In some embodiments, particulate aerogel material is held within container, wherein the container comprises a plurality of openings through which the particulate aerogel material can be transported. In some embodiments, the plurality of openings in the container may comprise one opening. In some embodiments, the plurality of openings in the container may comprise more than one opening. In some embodiments, the plurality of openings is located on one boundary of the container. In some embodiments, the plurality of openings is located on more than one boundary of the container. In some other embodiments, the openings are large enough to allow unimpeded transport of greater than 5%, greater than 10%, greater than 20%, greater than 30%, greater than 40%, greater than 50%, greater than 60%, greater than 70%, greater than 80%, greater than 90%, greater than 95%, or greater than 99% of the distribution of maximum cross-sectional dimensions of the particulate aerogel material. In some preferred embodiments, the openings are large enough to allow unimpeded transport of greater than 95% of the distribution of maximum cross-sectional dimensions of the particulate aerogel material.

In some embodiments, the plurality of openings is within a lid that is removable from the remainder of the container. In some embodiments, the lid screws on to the container. In some embodiments, the lid snaps on to the container. In some embodiments, the container has more than one lid. In some embodiments, the container has more than one lid with a plurality of openings. In some embodiments a plurality of openings, means more than 1 opening, more than 2 openings, more than 3 openings, more than 4 openings more than 5 openings, more than 10 openings, more than 20 openings, more than 30 openings, more than 40 openings, more than 50 openings, more than 100 openings, more than 200 openings, more than 300 openings, more than 400 openings, more than 500 openings, more than 1000 openings, more than 2000 openings, more than 3000 openings, more than 4000 openings, more than 5000 openings, or more than 10000 openings. In some embodiments, the density of the openings is at least $1/cm^2$, at least $2/cm^2$, at least $5/cm^2$, at least $10/cm^2$, at least $50/cm^2$, or more.

In some embodiments, the openings are within a wall of the container. In some embodiments, an opening is made in the container by puncturing, ripping, or tearing a wall of the container.

In some embodiments, the particulate aerogel material can leave the container when the container is inverted (e.g., via the force of gravity). In some embodiments, the particulate aerogel material can flow freely from openings in the container when the container is inverted. In some other embodiments, the particulate aerogel cannot flow freely from openings in the container when it is inverted. In some embodiments, the particulate aerogel material can be removed from the container using another object. In some embodiments, said object comprises a spoon. In some other embodiments, said object comprises a brush.

In some embodiments, the particulate hydrophobic aerogel material can leave the container when a relatively small amount of force is applied to the container. In some embodiments, the particulate aerogel material can leave the container when a pressure of less than 100 $N/cm^2$ is applied to the container. In some embodiments, applying force to the container comprises shaking the container. In some other embodiments, applying force to the container comprises squeezing the container. In some embodiments, applying force to the container comprises, hitting the container. In some embodiments, applying force to the container comprises stepping on the container. In some embodiments, applying force to the container comprises rubbing the container. In some embodiments, applying force to the container comprises flexing the container. In some embodiments, applying force to the container comprises rolling the container. In some embodiments, applying force to the container comprises, compressing a plug or plunger such that the particulate aerogel material is moved closer to the opening of the container.

In some embodiments, the particulate aerogel material can be dispersed within a liquid. In some embodiments, dispersing the particulate aerogel material in a liquid helps facilitate the application of an even layer of particulate aerogel material over human skin when compared to the application of particulate aerogel material not dispersed in a liquid. In some embodiments, the liquid is a lotion. In some embodiments, the lotion is easily absorbed into human skin and leaves behind a layer of particulate aerogel material. In some embodiments, the liquid is a paste. In some embodiments, the liquid is highly volatile. In some embodiments the highly volatile liquid quickly evaporates from human skin and leaves behind a layer of particulate aerogel material. In some embodiments, the liquid has a vapor pressure of at least 0.025 atm at STP (i.e., 1 atmosphere pressure and 25° C.). In some embodiments, the liquid has a vapor pressure of greater than 0.025 atm, greater than 0.03 atm, greater than 0.04 atm, greater than 0.05 atm, greater than 0.06 atm, greater than 0.07 atm, greater than 0.08 atm, greater than 0.09 atm, or greater than 0.1 atm at STP. In some embodiments, the highly volatile liquid comprises ethanol, acetone, water, or isopropanol.

In some embodiments, a kit is provided. A "kit," as used herein, typically defines a package or an assembly including one or more of the components disclosed herein, and/or other components associated with the embodiments disclosed here, for example, as previously described. A kit may, in some embodiments, include instructions in any form that are provided in connection with the components of the kit in such a manner that one of ordinary skill in the art would recognize that the instructions are to be associated with the components of the embodiments described herein. For instance, the instructions may include instructions for the use, modification, assembly, storage, or packaging of the components. In certain embodiments, the instructions include instructions for mixing, diluting, preserving, administering, and/or preparing compositions (e.g., particulate aerogel material, optional liquids, and the like) for use in association with the components of the kit. In some cases, the instructions may also include instructions for the use of the components or associated compositions, for example, for a particular use, e.g., for application to a handle. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the kit comprises a liquid and particulate aerogel material wherein, when the liquid and the particulate aerogel material are combined, the particulate aerogel material and the liquid form a combination that enhances friction between human skin and solid surfaces. In some embodiments, the particulate aerogel component, and the liquid component are held within two separate distinct containers. In some embodiments, the particulate aerogel material and the liquid component are held within the same container, but have a physical barrier separating the two components. In some embodiments, the physical barrier between the particulate aerogel material and the liquid can be broken, and the components can be combined by shaking the container. In some embodiments, the liquid component is a lotion. In some embodiments, the combination is a lotion. In some embodiments, the lotion is easily absorbed into human skin and leaves behind a layer of particulate aerogel material. In some embodiments, the liquid component is a paste. In some embodiments, the combination is a paste. In some embodiments, the liquid component is highly volatile. In some embodiments, the liquid has a vapor pressure of at least 0.025 atm at STP. In some embodiments, the liquid has a vapor pressure of greater than or equal to 0.025 atm, greater than or equal to 0.03 atm, greater than or equal to 0.04 atm, greater than or equal to 0.05 atm, greater than or equal to 0.06 atm, greater than or equal to 0.07 atm, greater than or equal to 0.08 atm, greater than or equal to 0.09 atm, or greater than or equal to 0.1 atm at STP. In some embodiments the highly volatile liquid quickly evaporates from human skin and leaves behind a layer of particulate aerogel material. In some embodiments, the particulate aerogel and liquid combination is a lotion. In some embodiments, the particulate aerogel and liquid combination is a paste.

In some embodiments, isolating the liquid from the particulate aerogel material increases the shelf-life of the kit. In some embodiments, the end-user is able to control the ratio of liquid to particulate aerogel material.

In some embodiments a combination is provided. In some embodiments, the combination comprises human skin and particulate aerogel material in contact with the human skin, and a solid surface in contact with the particulate aerogel material. In some embodiments, the particulate aerogel material is part of a layer. In some embodiments, the layer thickness is greater than or equal to 50 nanometers, and less than or equal to 1 millimeter.

In some embodiments an article is provided. In some embodiments, the article comprises a fibrous matrix and particulate aerogel material associated with the fibrous matrix, wherein the combination of the fibrous matrix and the aerogel material is in the form of a sheet. As used herein, a "sheet" refers to a form factor having a thickness dimension, a first dimension (e.g., a length dimension) orthogonal to the thickness dimension, and a second dimension (e.g., a depth dimension) orthogonal to the thickness dimension and the first dimension, where each of the first dimension and the second dimension are at least 10 times greater in size than the thickness dimension. In some embodiments, each of the first dimension and the second dimension are at least 100 times, at least 1000 times, or at least 10,000 times greater in size than the thickness dimension. When viewed from an angle parallel to the thickness, the sheet can have any of a variety of suitable shapes, including substantially rectangular, substantially circular, or any other shape. In some embodiments, the sheet is in the form of a roll. In some embodiments the roll comprises perforations between portions of the sheet. In some embodiments, the perforations allow for easy removal of one single-use portion of the sheet from the roll. In some embodiments, the sheet is one-time use. In further embodiments, the sheet is reusable. In some embodiments, the sheet is perforated in such a way as to provide greater than or equal to 10 single-use sections, greater than or equal to 20 single-use sections, greater than or equal to 30 single-use sections, greater than or equal to 40 single-use sections, greater than or equal to 50 single-use sections, or greater than or equal to 100 single-use sections.

In some embodiments, an article is provided. In some embodiments, the article comprises a container and a plurality of sheets within the container; wherein each of the sheets comprises a fibrous matrix and particulate aerogel material associated with the fibrous matrix. In some embodiments, the particulate aerogel material is present within the bulk of the fibrous matrix. In some embodiments, the particulate aerogel material is present on at least one external surface of the fibrous matrix. In some embodiments, the particulate aerogel material is present within the bulk of the fibrous matrix and on at least one external surface of the fibrous matrix. In some embodiments, at least one dimension of the sheet is greater than or equal to 100 micrometers and less than or equal to 1 millimeter. In some embodiments, the container comprises greater than or equal to 1 sheet, greater than or equal to 5 sheets, greater than or equal to 10 sheets, greater than or equal to 20 sheets, greater than or equal to 30 sheets, greater than or equal to 40 sheets, greater than or equal to 50 sheet, or greater than or equal to 100 sheets.

FIG. 1 depicts a magnified view of an aerogel particle, according to certain embodiments. The schematic shows an aerogel particle 1 showing the primary porosity 2 and secondary porosity 3. In some embodiments, the aerogel particle comprises an inorganic oxide aerogel. In certain embodiments, the inorganic oxide aerogel comprises an oxide of silicon, aluminum, titanium, hafnium, zirconium, chromium, niobium, tantalum, iron, vanadium, neodymium, samarium, holmium, zinc, magnesium, calcium, and/or erbium. In some preferred embodiments the inorganic oxide aerogel comprises silica. In further preferred embodiments, the silica comprises a hydrophobic silica.

Figure 2:
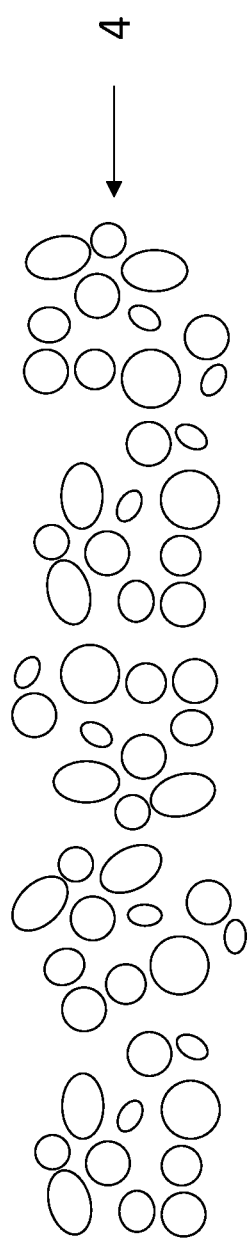
FIG. 2 depicts particulate aerogel material of varying size and shape, according to certain embodiments.

FIG. 2 depicts particulate aerogel material 4 of varying size and shape, according to certain embodiments.

Figure 3:
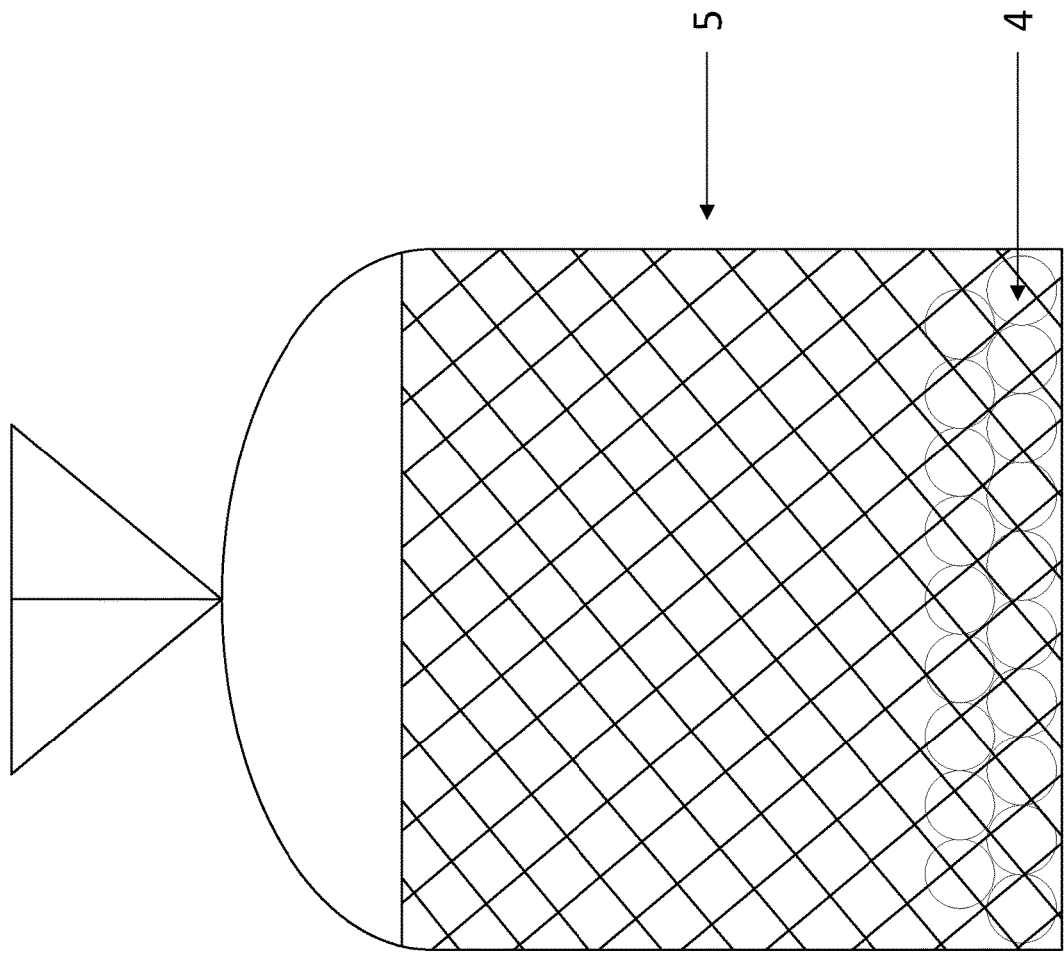
FIG. 3 depicts a porous flexible container containing particulate aerogel material, according to certain embodiments.

FIG. 3 depicts a porous flexible container 5 comprising particulate aerogel material 4, according to certain embodiments. In some embodiments, the flexible container is porous and permits transport of the particulate aerogel through at least part of the porous boundary upon application of force to the flexible container. In certain embodiments, applying force to the flexible container fractures the particulate aerogel material within the flexible container, and the new, smaller particulate aerogel material can leave at least part of the porous boundary of the flexible container.

Figure 4:
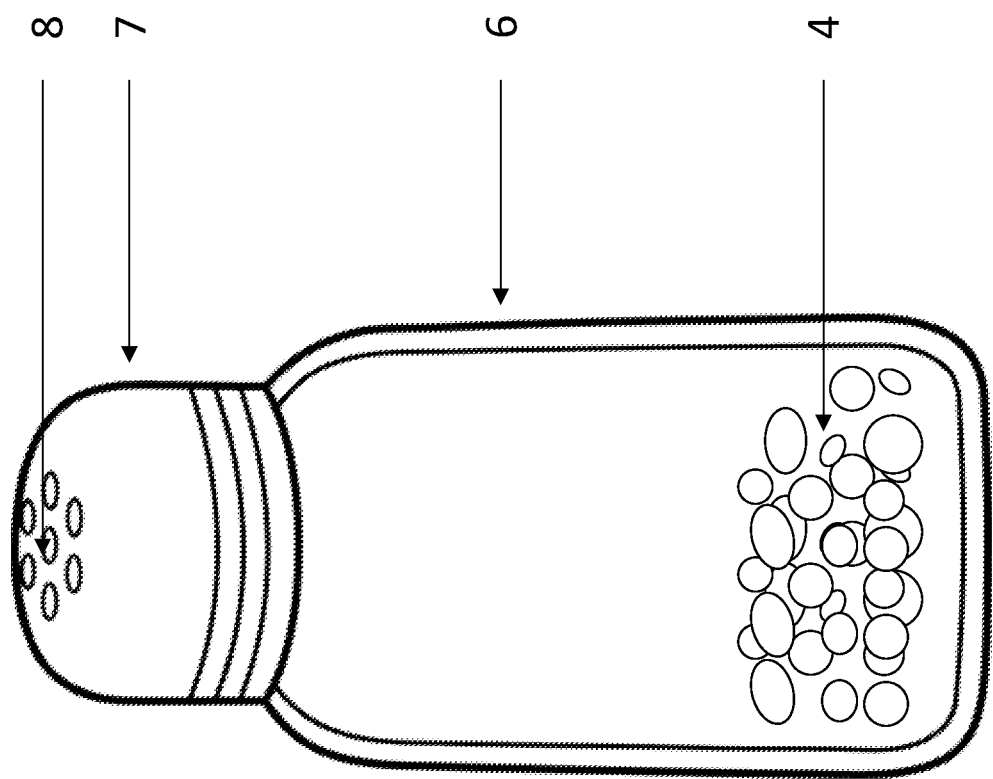
FIG. 4 depicts a container containing particulate aerogel material and comprising a removable lid with a plurality of openings, according to certain embodiments.

FIG. 4 depicts a container 6 comprising particulate aerogel material 4 and a removable lid 7 with a plurality of openings 8 through which the particulate aerogel material can be transported, according to certain embodiments. In certain embodiments, the particulate aerogel material can leave the plurality of openings when the container is inverted. In certain embodiments, the particulate aerogel material can leave the plurality of openings when a force is applied to the container.

Figure 5:
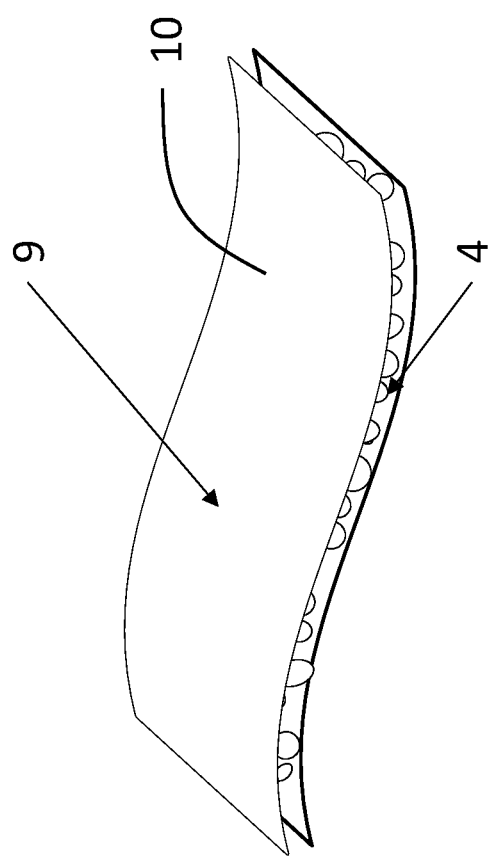
FIG. 5 depicts a sheet comprising a combination of a fibrous matrix and associated particulate aerogel material, according to certain embodiments.

FIG. 5 depicts sheet 9 which comprises of a combination of a fibrous matrix 10 and associated particulate aerogel material 4, according to certain embodiments, wherein the particulate aerogel material is present within the bulk of the fibrous matrix 10 and at least one dimension of the sheet 9 is greater than or equal to 100 micrometers and less than or equal to 1 millimeter.

Figure 6:
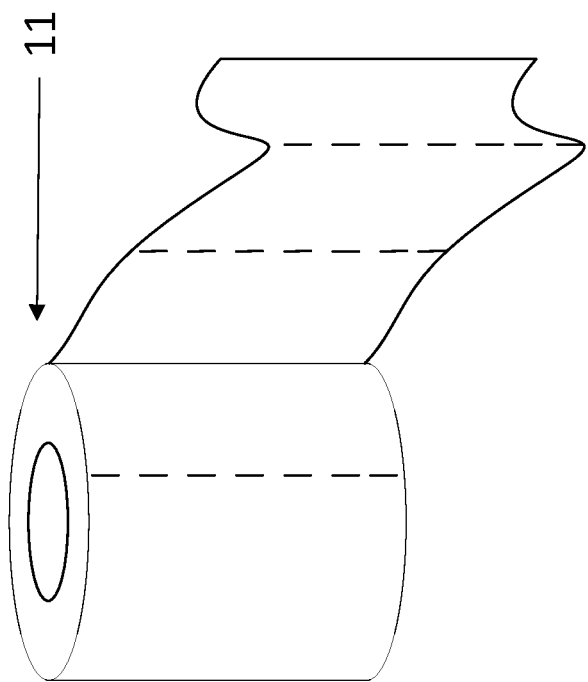
FIG. 6 depicts a roll of the fibrous sheet from FIG. 5 wherein the sheet comprises perforations.

FIG. 6 depicts a continuous roll 11 of perforated sheets of the aforementioned fibrous sheets 10.

Figure 7:
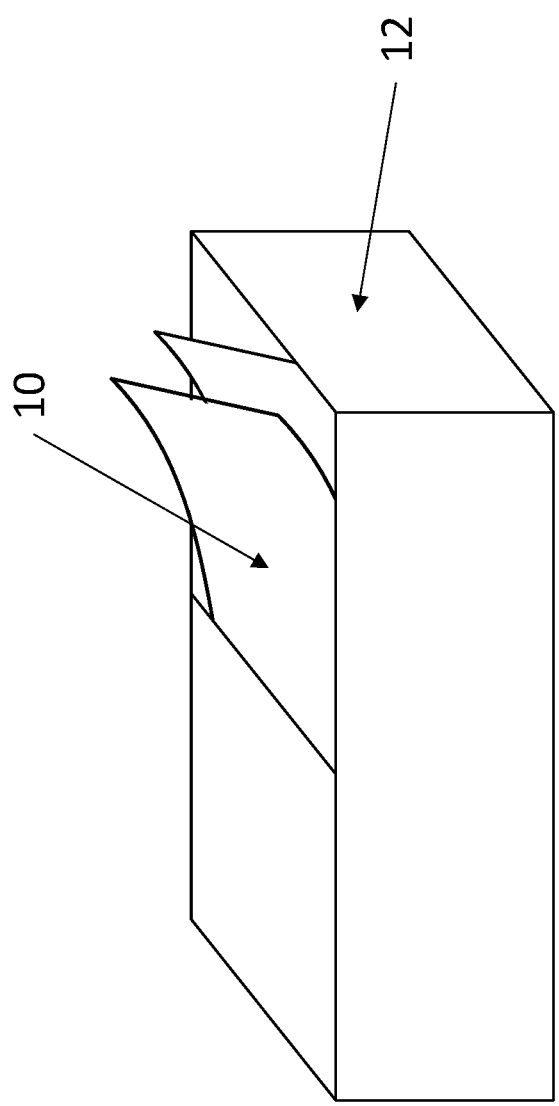
FIG. 7 depicts a container comprising the fibrous sheets from FIG. 5, according to certain embodiments.

FIG. 7 depicts a container 12 containing the aforementioned fibrous sheets 10, wherein each sheet comprises particulate aerogel material 4, according to certain embodiments.

Figure 8A:
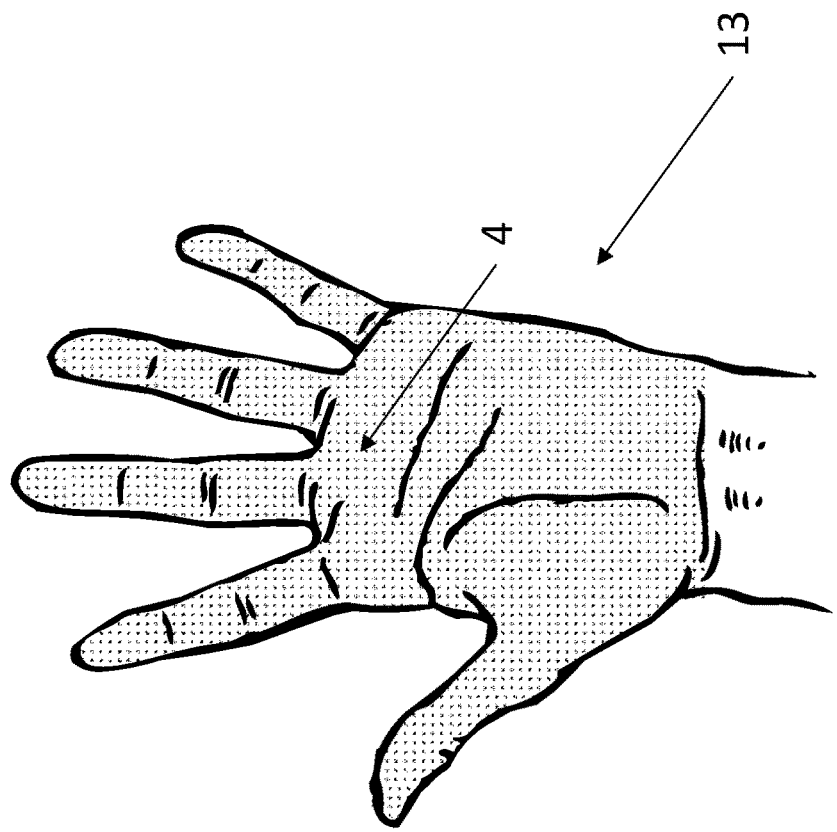
FIG. 8A depicts a human hand comprising a layer of particulate aerogel material covering at least a portion of its surface area, according to certain embodiments.

FIG. 8A depicts a human hand 13 comprising a layer of particulate aerogel material 4 covering at least a fraction of its surface area, according to certain embodiments, wherein the average layer thickness is greater than or equal to 50 nanometers, and less than or equal to 1 millimeter. In some embodiments, the particulate aerogel material can cover at least 25%, at least 40%, at least 50%, at least 75%, at least 90%, at least 95%, at least 99% or all of the interior surface area of a human hand. In some embodiments, the particulate aerogel material can form a conformal coating over at least 25%, at least 40%, at least 50%, at least 75%, at least 90%, at least 95%, at least 99% or all of the interior surface area of a human hand.

Figure 8B:
FIG. 8B depicts the particulate aerogel material-layered hand from FIG. 8A in contact with a solid surface, according to certain embodiments.

FIG. 8B depicts the previously mentioned particulate aerogel material-layered hand 13 in contact with a solid surface 14, wherein the solid surface can be part of a door knob, helmet, other human skin, helicopter, rope, ladder, camera, wood, metal, torch, plastic, ceramic, composite, shoe, glove, sock, chain, microphone, cardboard box, Styrofoam box, cooler, umbrella, smartphone, computer, tablet, furniture, door, face, wall, window, directional pad, floor, or ground, according to certain embodiments.

Figure 8C:
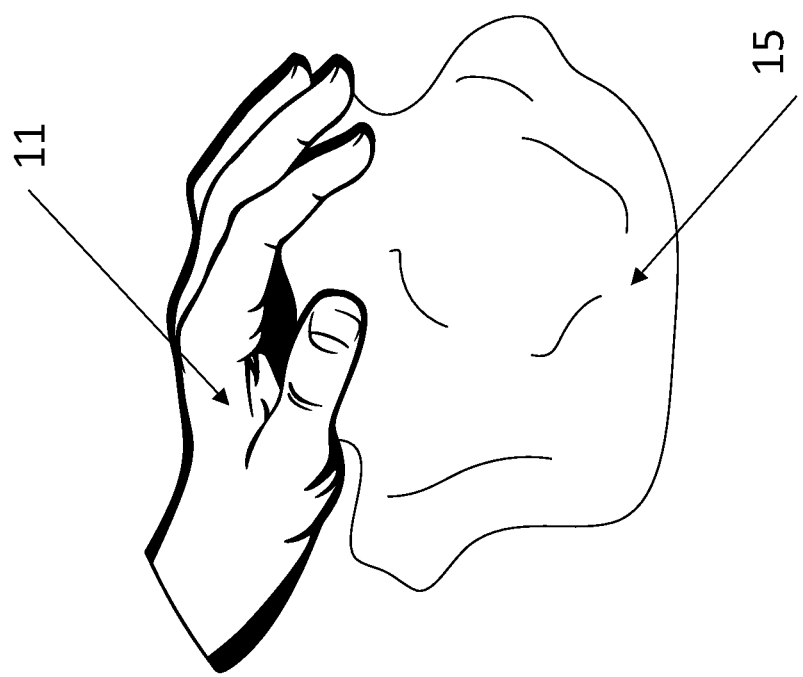
FIG. 8C depicts the particulate aerogel material-layered hand from FIG. 8A in contact with an object, such as a rock, according to certain embodiments.

FIG. 8C depicts the previously mentioned particulate aerogel material-layered hand 13 in contact with an object, wherein the various objects can be parts of a grippable object 15, such a rock, according to certain embodiments.

Figure 8D:
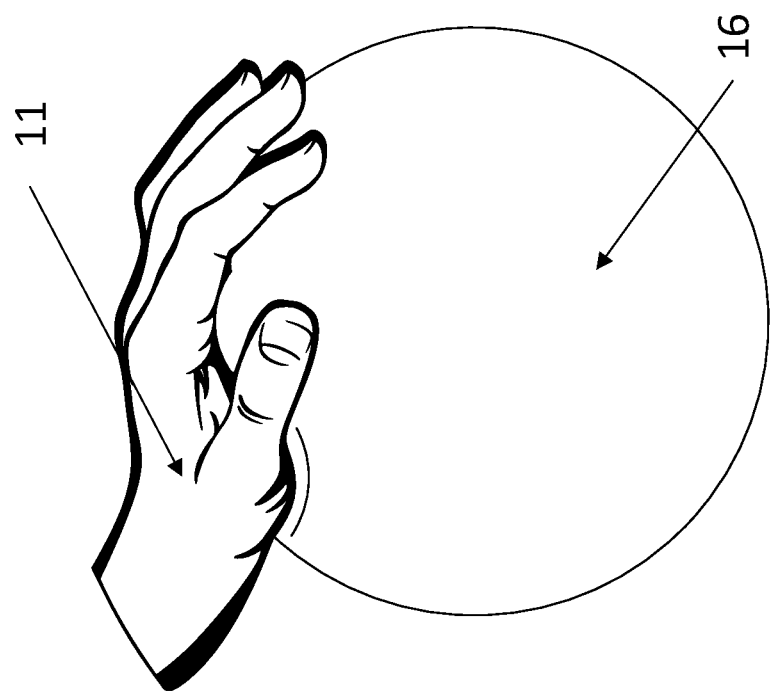
FIG. 8D depicts the particulate aerogel material-layered hand from FIG. 8A in contact with an object, such as a ball, according to certain embodiments.

FIG. 8D depicts the previously mentioned particulate aerogel material-layered hand 13 in contact with an object, wherein the various objects can be parts of a grippable object 16, such a ball, according to certain embodiments.

Figure 8E:
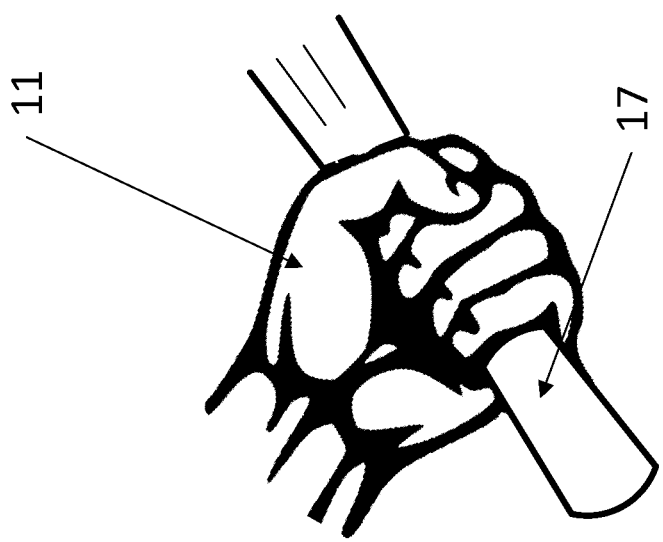
FIG. 8E depicts the particulate aerogel material-layered hand from FIG. 8A in contact with an object, such as a handle, according to certain embodiments.

FIG. 8E depicts the previously mentioned particulate aerogel material-layered hand 13 in contact with an object, wherein the various objects can be parts of a gripable object 17, such as a handle, a grip, a musical instrument or its accessories, sports equipment, a handlebar, a steering wheel, a tool, a video game controller, a firearm, weightlifting equipment, gymnastics equipment, video camera, boom mic, switch, parachute, hot air balloon, katana, nunchaku, sai, shuriken, taser, spray can, megaphone, boot, crutches, walker, cane, backpack, shopping bag, disk, tray, another human, animal, wheelchair, knob, or button, according to certain embodiments. In some embodiments, the hand can extend around at least 50%, at least 75%, at least 90%, at least 95%, at least 99%, or more of a circumference of a portion of the object. For example, in FIG. 8E, hand 11 extends around 100% of the circumference of a middle portion of the handle shown in FIG. 8E.

Figure 9:
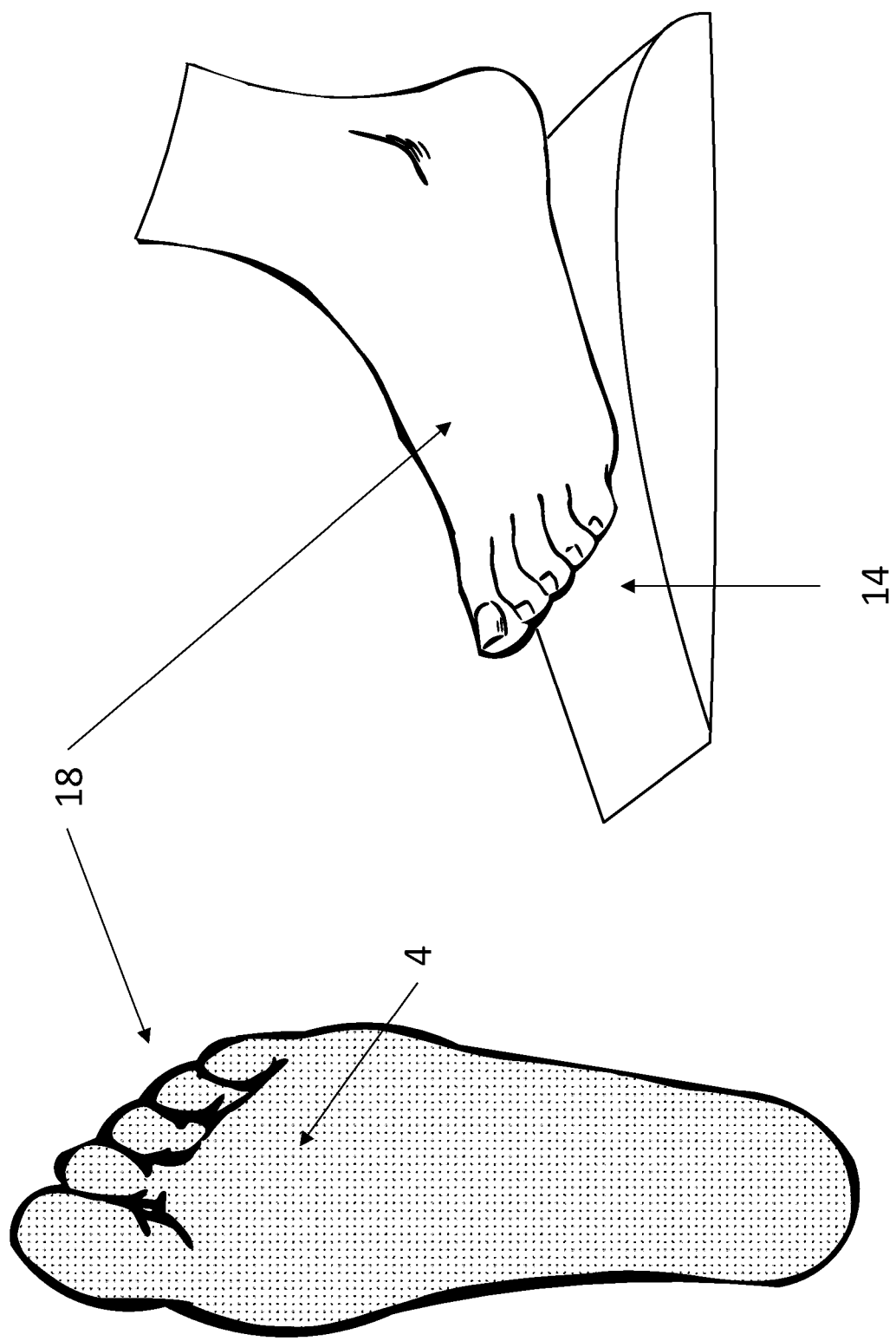
FIG. 9 depicts a human foot comprising a layer of particulate aerogel material covering at least a portion of its surface area, according to certain embodiments.

FIG. 9 depicts a human foot 18 comprising a layer of particulate aerogel material 4 covering at least a fraction of its surface area, according to certain embodiments, wherein the average layer thickness is greater than or equal to 50 nanometers, and less than or equal to 1 millimeter. The right-hand side depicts the previously mentioned aerogel-layered foot in contact with a surface 14 such as a mat, according to certain embodiments. In some embodiments, the particulate aerogel material can cover at least 25%, at least 40%, at least 50%, at least 75%, at least 90%, at least 95%, at least 99% or all of the bottom surface area of a human foot. In some embodiments, the particulate aerogel material can form a conformal coating over at least 25%, at least 40%, at least 50%, at least 75%, at least 90%, at least 95%, at least 99% or all of the bottom surface area of a human foot.

FIGS. 10A-10F depict various forms of contact between human skin 19, particulate aerogel material 4, and a solid surface 14, according to certain embodiments. In some embodiments, friction between the human skin 19 and the solid surface 14, when the particulate aerogel material 4 is present between the human skin and the solid surface, is higher than it would be under otherwise identical conditions without the particulate aerogel.

Figure 10A:
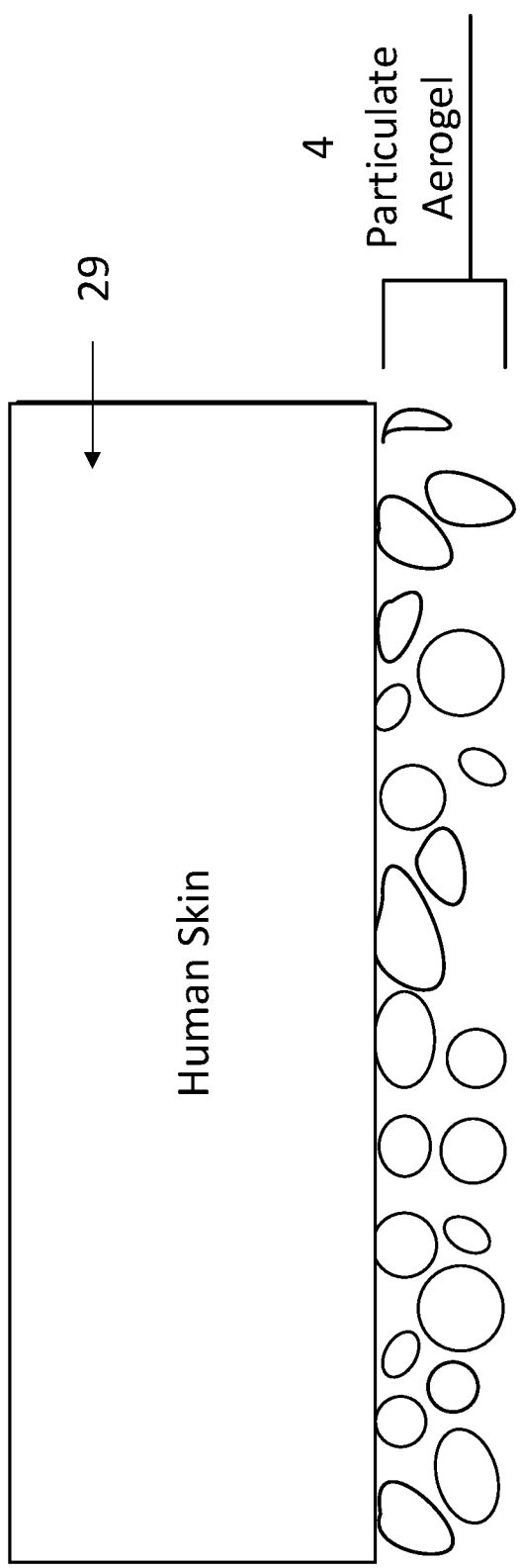
FIG. 10A depicts a layer of particulate aerogel material on human skin, according to certain embodiments.

FIG. 10A depicts a layer of particulate aerogel material 4 in direct contact with human skin 29, according to certain embodiments.

Figure 10B:
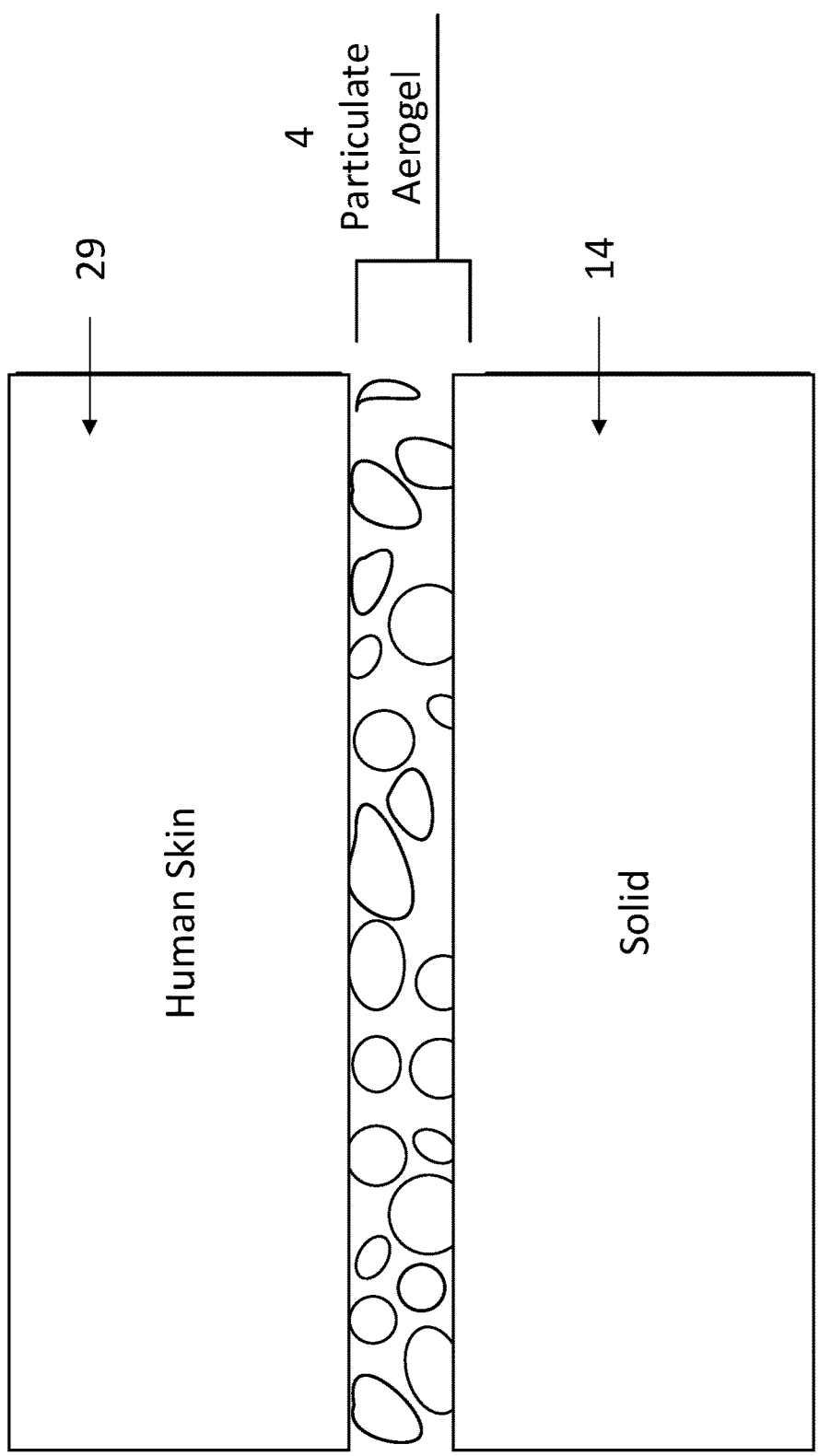
FIG. 10B depicts a layer of particulate aerogel material between human skin and a surface, according to certain embodiments.

FIG. 10B depicts a layer of particulate aerogel material 4 in direct contact with both human skin 29 and surface of solid 14, with the particulate aerogel material positioned between human skin 19 and the surface of solid 14, according to certain embodiments.

Figure 10C:
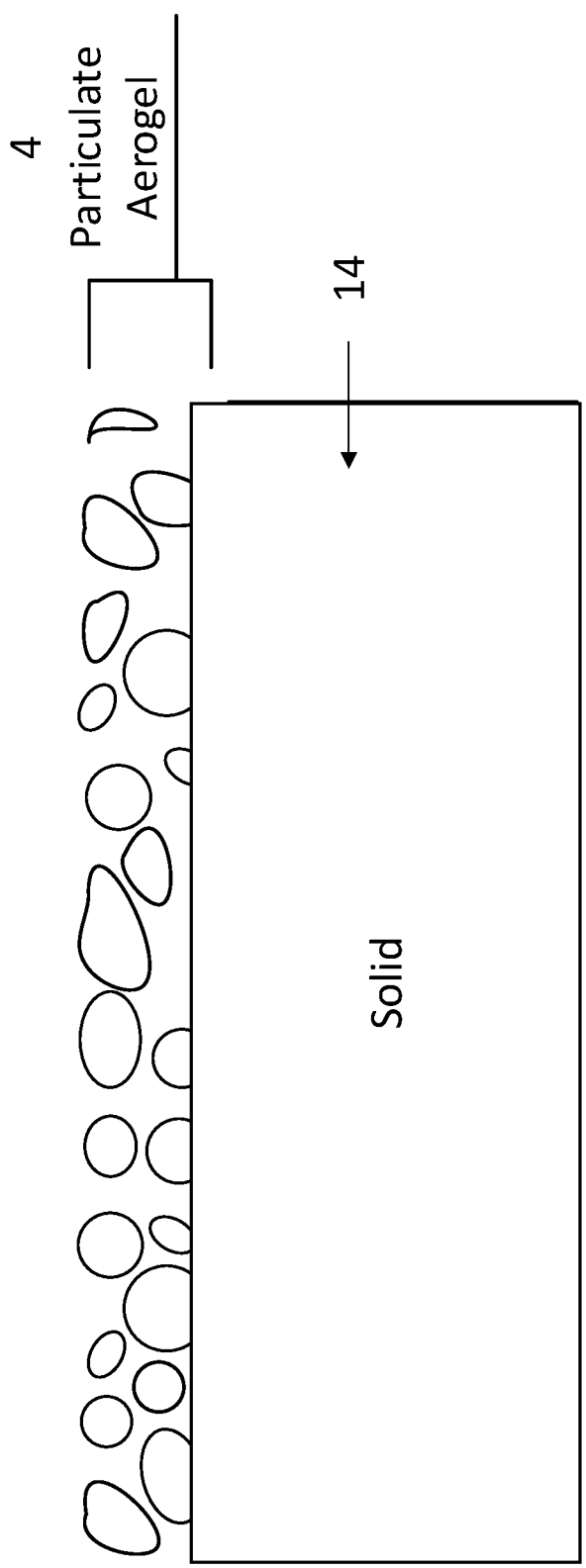
FIG. 10C depicts a layer of particulate aerogel material on a surface, according to certain embodiments.

FIG. 10C depicts a layer of particulate aerogel material 4 in direct contact with a surface of solid 14, according to certain embodiments.

Figure 10D:
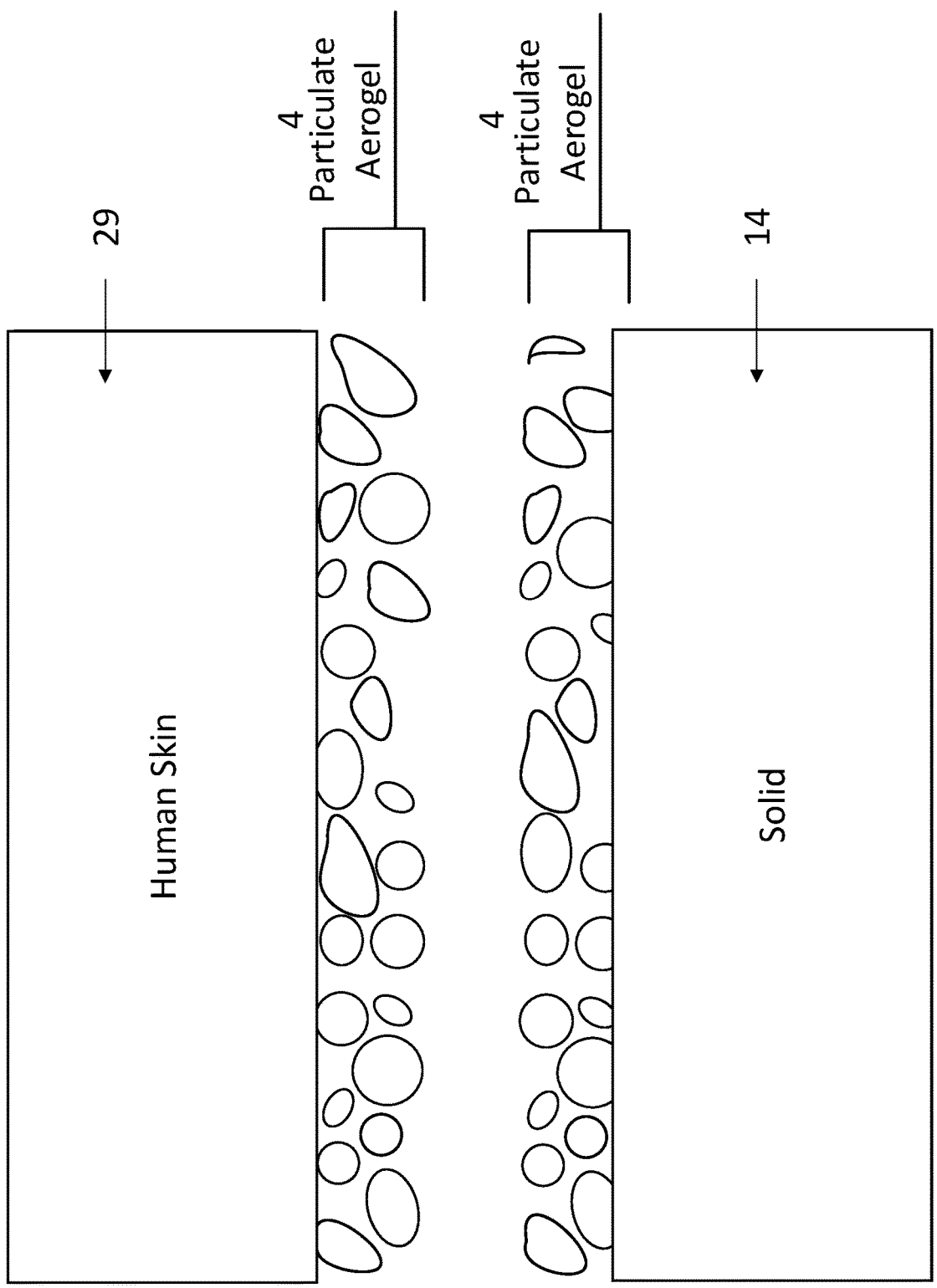
FIG. 10D depicts a layer of particulate aerogel material on both human skin and a surface coming into contact with one another, according to certain embodiments.

FIG. 10D depicts a layer of particulate aerogel material 4 on both a surface of solid 14 and human skin 29 coming into contact with one another, according to certain embodiments.

Figure 10E:
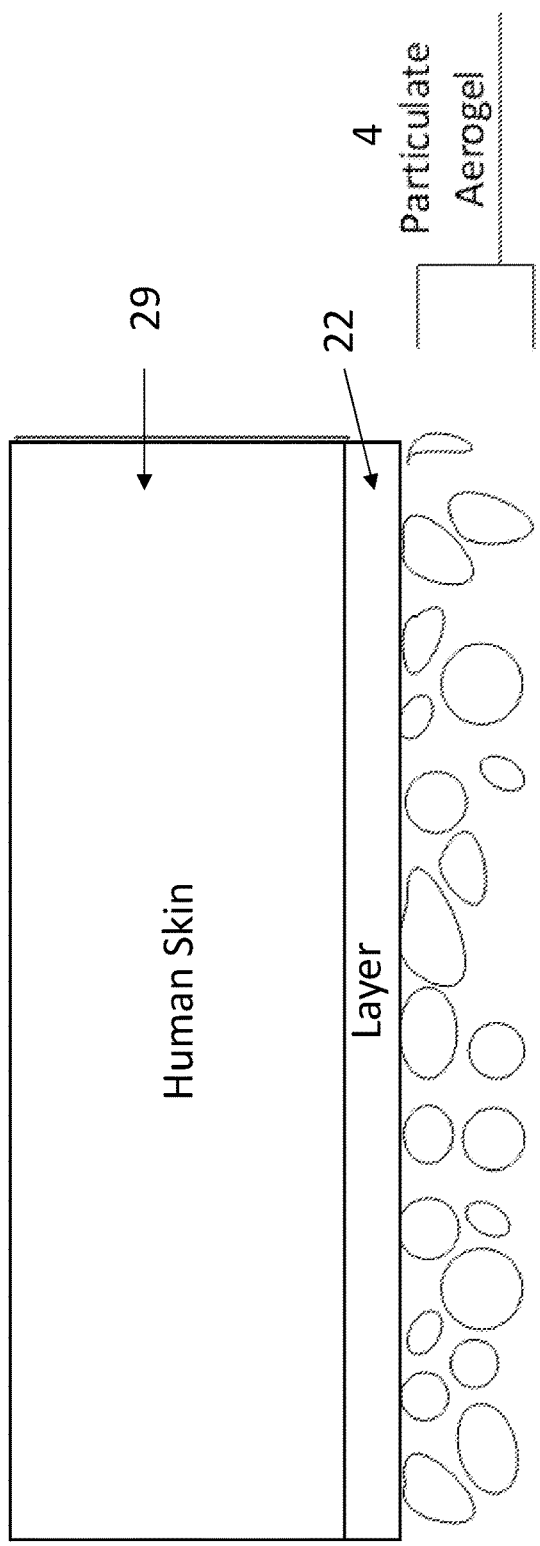
FIG. 10E depicts a layer of particulate aerogel material in indirect solid contact with human skin, according to certain embodiments.

FIG. 10E depicts a layer of particulate aerogel material 4 in indirect solid contact with human skin 29, with layer 22 between particulate aerogel material 4 and human skin 29, according to certain embodiments.

Figure 10F:
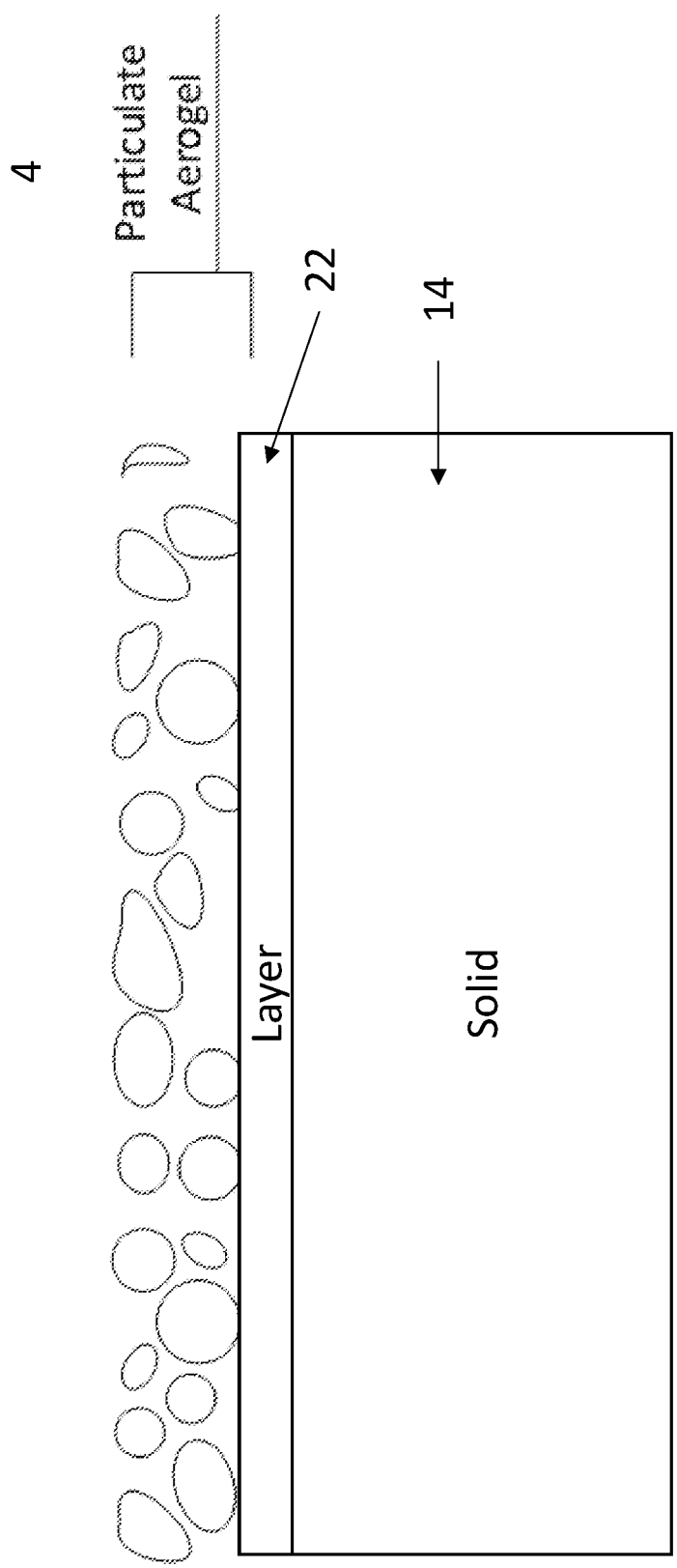
FIG. 10F depicts a layer of particulate aerogel material in indirect solid contact with a surface of a solid, according to certain embodiments.

FIG. 10F depicts a layer of particulate aerogel material 4 in indirect solid contact with a surface of solid 14, with layer 22 between particulate aerogel material 4 and solid 14, according to certain embodiments.

Figure 11:
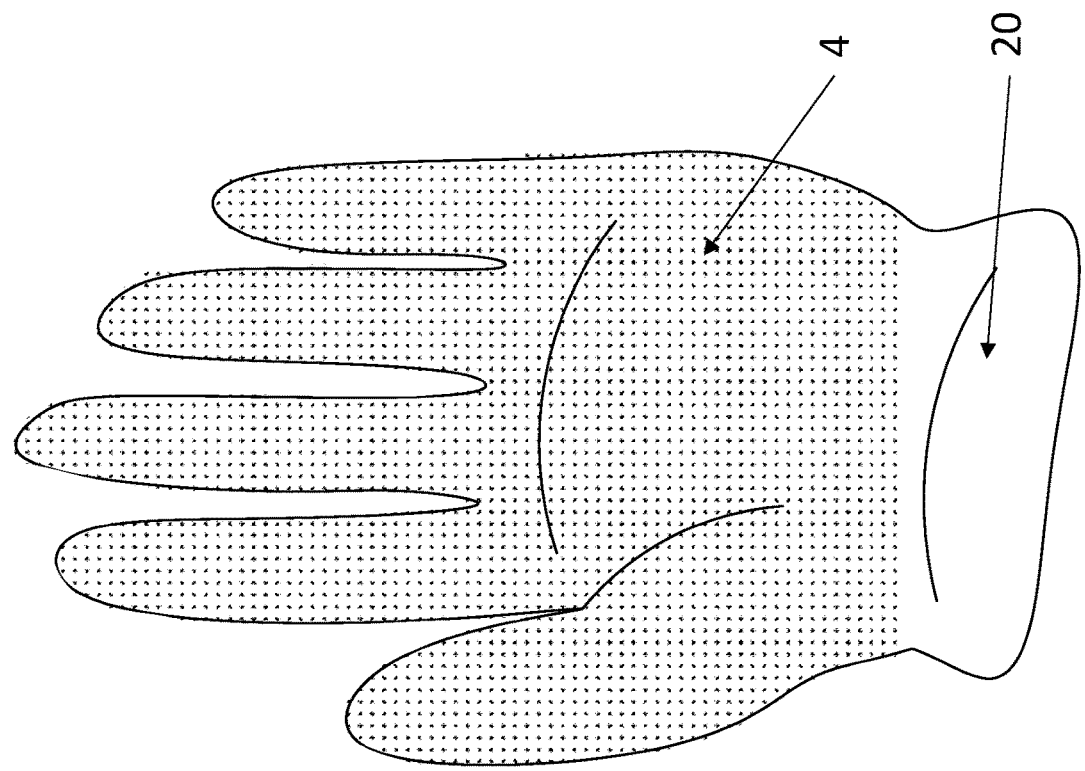
FIG. 11 depicts a glove comprising a layer of particulate aerogel material covering at least a portion of its external surface area, according to certain embodiments.

FIG. 11 depicts a glove 20 comprising a layer of particulate aerogel material 4 covering at least a fraction of its external surface area, according to certain embodiments.

Figure 12:
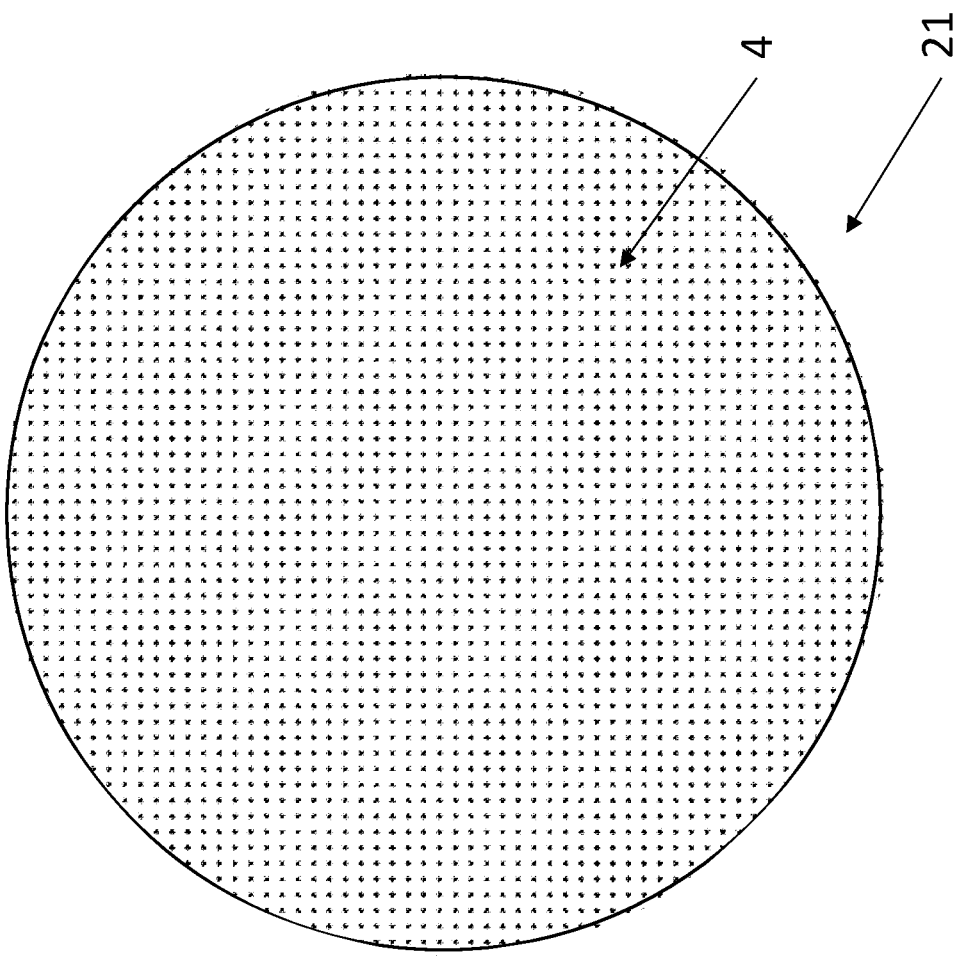
FIG. 12 depicts a ball comprising a layer of particulate aerogel material covering at least a portion of its external surface area, according to certain embodiments.

FIG. 12 depicts ball 21 comprising a layer of particulate aerogel material 4 covering at least a fraction of its external surface area, according to certain embodiments.

Figure 13:
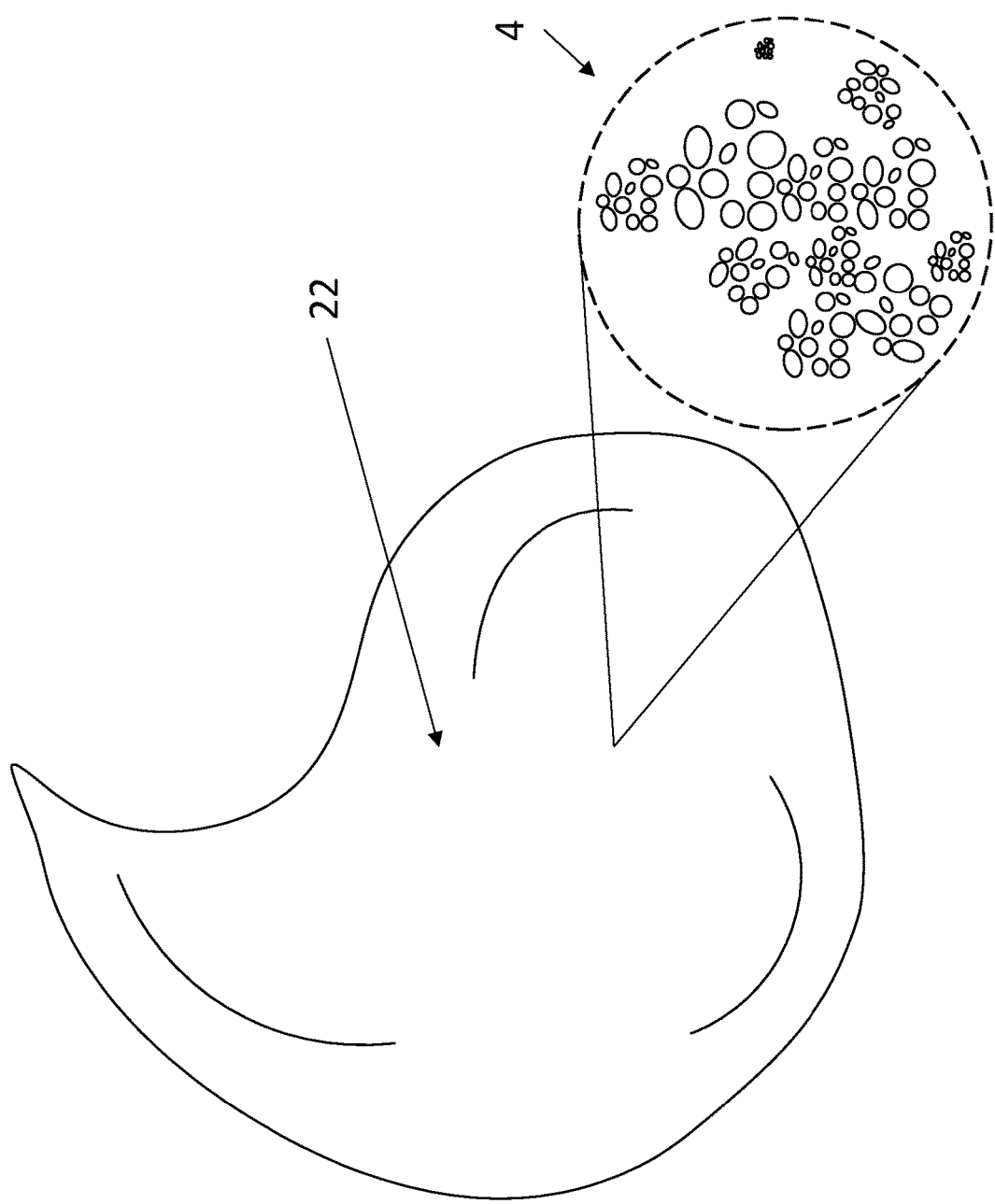
FIG. 13 depicts a liquid comprising particulate aerogel material dispersed within the liquid, according to certain embodiments.

FIG. 13 depicts a liquid 22 comprising particulate aerogel material 4 dispersed within the liquid, according to certain embodiments, wherein the liquid can be a lotion or paste and has a vapor pressure of at least 0.025 atm at STP, that, when applied to human skin, will deposit a layer of particulate aerogel material.

EXAMPLES

The following examples are intended to illustrate certain embodiments of the present invention, but do not exemplify the full scope of the invention.

Example 1

Application of Particulate Aerogel Material to an Athlete's Hands by Rubbing Particulate Aerogel Material Between them A subject was asked to stand fully upright and hold a weight in one hand, with their arm fully extended and parallel to their body, for as long as possible until they felt they could no longer hold the weight due to exhaustion. The subject was a 35-year-old male of moderate athletic build, 68" inches in height, weighing 100 kg. The weight was a 90-lb dumbbell with a knurled stainless-steel handle. The subject was asked to perform the test above. The time from first picking up the dumbbell to having to drop the dumbbell was measured with a stopwatch and recorded. The subject was then allowed to rest for 60 minutes.

After resting for 60 minutes, 10 mL of particulate aerogel material was poured into the subject's hand. The particulate aerogel material exhibited a particle size distribution such that at least 50% of the particles had a maximum cross-sectional dimension of between 0.7 mm and 1.2 mm. The particulate aerogel material comprised trimethylsilylated silica aerogel. The subject then rubbed both hands together with open palms such that the particulate aerogel material coated at least a portion of the skin on their hands. The subject was then asked to repeat the test above, using the same hand as they used in the first test. The time from first picking up the dumbbell to having to drop the dumbbell was measured with a stopwatch and recorded.

The time recorded in the first test, without particulate aerogel material, was 59 seconds. The time recorded in the second test, after application of particulate aerogel material, was 77 seconds.

Example 2

Application of Particulate Aerogel Material to an Athlete's Hands by Squeezing a Porous Flexible Bag A subject performed the same test as described in Example 1. Rather than applying the particulate aerogel material in the manner described in Example 1, the subject squeezed a flexible, porous bag filled with particulate aerogel material, which caused particulate aerogel material to be pushed out of the bag though its porous surface, onto the hands of the subject. All other test conditions and results were the same.

Example 3

Application of Particulate Aerogel Material to an Athlete's Hands by Rubbing a Fibrous Sheet Comprising Particulate Aerogel Material on them A subject performed the same test as described in Example 1. Rather than applying the particulate aerogel material in the manner described in Example 1, the subject rubbed both hands with a fibrous sheet comprising particulate aerogel material. All other test conditions and results were the same.

Example 4

Application of Particulate Aerogel Material to an Athlete's Hands by Dispensing Particulate Aerogel Material from a Bottle with a Perforated Lid A subject performed the same test as described in Example 1. Rather than dispensing a volume of particulate aerogel material into his hands, the subject used a bottle with a perforated lid to sprinkle particulate aerogel material onto his hands. All other test conditions and results were the same.

Example 5

Application of Particulate Aerogel Material to a Powerlifter's Hands by Rubbing Particulate Aerogel Material Between them A powerlifter was asked to count and record the number of times they applied chalk to their hands during a workout. The workout comprised five sets. Each set comprised five repetitions. Each repetition comprised one deadlift of 145 kg. The powerlifter reported applying chalk to her hands before each set, in order feel that she was achieving maximum performance.

The powerlifter was asked to repeat the same workout on a different day. On the second day, before starting her workout, the powerlifter applied particulate aerogel material to her hands using the particulate aerogel material and method of Example 1. She did not apply any chalk on the second day. The powerlifter reported that using this technique she only needed to apply the particulate aerogel material to her hands twice during the workout (once at the beginning of the workout and one additional time) to achieve an equivalent level of performance.

Example 6

Application of Particulate Aerogel Material to an Athlete's Hands by Rubbing Particulate Aerogel Material Between them An athlete was asked to grasp a pull-up bar with both hands pull-up position (i.e., at shoulder width, with hands pronated, arms fully extended overhead). The athlete was asked to hang from the pull-up bar in this position until she could no longer grip the bar. She reported sustaining this position for 32 seconds. The athlete was asked to wait one hour, then apply particulate aerogel material using the particulate aerogel material and method outlined in Example 1, and then repeat the test. The athlete reported sustaining the position for 40 seconds in this case.

Example 7

Application of Particulate Aerogel Material Comprising Trimethylsilylated Alumina Aerogel Particles to an Athlete's Hands by Rubbing Particulate Aerogel Material Between them A subject performed the same test as described in Example 1. The particulate aerogel material comprised trimethylsilylated alumina aerogel rather than trimethylsilyated silica aerogel. All other test conditions and results were the same.

Example 8

Application of Particulate Aerogel Material to a Golfer's Hands by Rubbing Particulate Aerogel Material Between them A golfer applied particulate aerogel material to their hands using the particulate aerogel material and method of Example 1, and played 18 holes of golf. The golfer reported typically wearing a glove on the non-dominant hand while playing golf, but did not wear the glove during this test. The golfer reported less perspiration on his hands than without use of the particulate aerogel material. The golfer reported grip was equivalent to that experienced when wearing a glove. Furthermore, the golfer reported better dexterity, feel (i.e., more nuanced tactile feedback during ball-strike) than when wearing a glove.

Example 9

Application of Particulate Aerogel Material to a Paddle Tennis Player's Hands by Rubbing Particulate Aerogel Material Between them A paddle tennis player applied particulate aerogel material before a match to their hands using the particulate aerogel material and method of Example 1. After the match, the paddle tennis player reported that their hands were significantly less sweaty than usual over the course of the match. The paddle tennis player described their grip on the paddle as significantly improved. Furthermore, they reported having to re-apply the particulate aerogel material infrequently, with a maximum frequency of between each set.

Example 10

Application of Particulate Aerogel Material to a Tennis Player's Hands by Rubbing Particulate Aerogel Material Between them A non-professional female tennis player playing in a competitive league applied particulate aerogel material to her hands before a match using the particulate aerogel material and method in Example 1. After the match, the tennis player reported that her hands were significantly less sweaty than usual over the course of the match. The tennis player described her grip on the racket as significantly improved. Furthermore, she reported having to re-apply the particulate aerogel material infrequently, with a maximum frequency of between each set.

Example 11

Application of Particulate Aerogel Material to a Singer's Hands by Rubbing Particulate Aerogel Material Between them A singer applied particulate aerogel material to her hands before a concert using the particulate aerogel material and method in Example 1. The singer reported that she was able to maintain a better grip on the microphone during her performance. She reported that she had to take few breaks to wipe sweat from her hands.

Example 12

Application of Particulate Aerogel Material to a Guitar Player's Hands by Rubbing Particulate Aerogel Material Between them An electric guitar player applied particulate aerogel material to his hands using the particulate aerogel material and method in Example 1. The guitar player typically applied chalk in a similar manner to his hands before performances in order to maintain a more secure grip on the neck of his instrument and his guitar pick. Using particulate aerogel materials instead, he reported that his hands stayed drier and had better grip for longer. Furthermore, he reported the particulate aerogel material did not shed from his hands and clog his strings and pickups the way chalk normally did.

Example 13

Application of Particulate Aerogel Material to a Drummer's Drumsticks by Rubbing Particulate Aerogel Material Between them A drummer applied particulate aerogel material to his sticks before a performance by pouring an amount of the particulate aerogel material into his hands, then dragging his drumstick through the material. The drummer reported that his hands were dryer during the performance, and that as a result he dropped fewer drumsticks.

Example 14

Application of Particulate Aerogel Material to a U.S. Army Special Forces Mountain Team Member's Hands by Rubbing Particulate Aerogel Material Between them A member of the U.S. Army Special Forces Mountain Team applied particulate aerogel material to his hands before a training exercise using the particulate aerogel material and method of Example 1. He reported enhanced grip on his firearm, rope, and rock surfaces. He reported that he preferred the particulate aerogel material to chalk because he could achieve the same effect while using less material and reapplying less often.

Example 15

Application of Particulate Aerogel Material to a Baseball by Rubbing Particulate Aerogel Material on it A pitcher for a baseball team applied particulate aerogel material to a new, unused baseball before a game by pouring the particulate aerogel material into his hand, and then rubbing the ball in his hands vigorously to coat all surfaces, then brushing the excess off with a clean towel. The pitcher reported that the ball felt soft and dry in his hand, and that it maintained this feeling longer before having to be replaced. He reported that the "new" appearance of the ball was maintained longer, and that after the ball touched wet grass it felt drier than without the particulate aerogel material. Furthermore, he reported that his throws were more consistent after applying the particulate aerogel material.

Example 16

Application of Particulate Aerogel Material to a Baseball Catcher's Hands by Rubbing Particulate Aerogel Material Between them A catcher for a baseball team applied particulate aerogel material to his hands before a game using the particulate aerogel material and method of Example 1. He reported the same impressions as the pitcher in Example 15.

Example 17

Application of Particulate Aerogel Material to a Basketball Player's Hands by Rubbing Particulate Aerogel Material Between them A basketball player applied particulate aerogel material to her hands before a game using the particulate aerogel material and method of Example 1. She reported that her hands were less sweaty than usual, and that her grip on the basketball while dribbling, passing, and shooting was enhanced.

Example 18

Application of Particulate Aerogel Material to an American Football Player's Hands by Rubbing Particulate Aerogel Material Between them A wide receiver for an American football team applied particulate aerogel material to his hands before practice using the particulate aerogel material and method of Example 1. He reported more successfully received passes, and improved grip on the ball while running.

Example 19

Application of Particulate Aerogel Material to a Football by Rubbing Particulate Aerogel Material on it A quarterback for an American football team applied particulate aerogel material to the ball he was using according to the method of Example 15 before practice. He reported improved grip on the ball and more consistent throwing.

Example 20

Application of Particulate Aerogel Material to a Gymnast's Feet by Rubbing Particulate Aerogel Material on them A male gymnast competing in the vaulting event applied particulate aerogel material to his feet before a competition by pouring 10 mL of the particulate aerogel material into his hands, and then rubbing the particulate aerogel material on the sole of each of his feet. He reported improved height and landing, as well as more consistent rotation.

Example 21

Application of Particulate Aerogel Material to a Gymnast's Feet by Stepping on a Flexible Porous Bag Comprising Particulate Aerogel Material A male gymnast competing in the vaulting event applied particulate aerogel material to his feet before a competition by repeatedly stepping on a flexible porous bag comprising particulate aerogel material. He reported improved height and landing, as well as more consistent rotation.

Example 22

Application of Particulate Aerogel Material to a Gymnast's Hands by Rubbing Particulate Aerogel Material Between them A female gymnast competing in the uneven bars event applied particulate aerogel material to her hands before a competition using the particulate aerogel material and method of Example 1. She reported improved grip on the bars during her routine.

Example 23

Application of Particulate Aerogel Material to a Carpenter's Hands by Rubbing Particulate Aerogel Material Between them A carpenter applied particulate aerogel material to her hands using the particulate aerogel material and method of Example 1 before a job building a wood-frame house. She reported enhanced grip on her hammer and other hand tools. The carpenter reported that this increased her efficiency as a result, as well as decreased injuries and damage to tools due to dropping.

Various Embodiments

The following outlines various examples of embodiments of inventions disclosed herein. The following are intended to illustrate certain embodiments of the present invention, but do not exemplify the full scope of the invention.

In some aspects, methods are provided. In some embodiments, the method, comprises establishing direct contact and/or indirect solid contact between human skin, a particulate aerogel material, and a solid surface, wherein the particulate aerogel material is between the human skin and the solid surface [Embodiment 1].

In some cases of Embodiment 1, the particulate aerogel material is hydrophobic [Embodiment 2].

In some cases of any one of Embodiments 1-2, the establishing comprises: establishing direct contact or indirect solid contact between the human skin and the particulate aerogel material; and subsequently establishing direct contact or indirect solid contact between the solid surface and the particulate aerogel material that is in direct contact or indirect solid contact with the human skin [Embodiment 3].

In some cases of any one of Embodiments 1-2, the establishing comprises: establishing direct contact or indirect solid contact between the solid surface and the particulate aerogel material; and subsequently establishing direct contact or indirect solid contact between the human skin and the particulate aerogel material that is in direct contact or indirect solid contact with the solid surface [Embodiment 4].

In some cases of any one of Embodiments 1-4, the human skin is in direct contact with the particulate aerogel material [Embodiment 5].

In some cases of any one of Embodiments 1-4, the human skin is in indirect solid contact with the particulate aerogel material [Embodiment 6].

In some cases of Embodiment 6, an apparel article is located between the human skin and the particulate aerogel material [Embodiment 7].

In some cases of any one of Embodiments 1-7, the average maximum cross-sectional dimension of the particulate aerogel material is less than or equal to 1 centimeter [Embodiment 8].

In some cases of any one of Embodiments 1-7, the average maximum cross-sectional dimension of the particulate aerogel material is greater than or equal to 50 nanometers and less than or equal to 1 centimeter [Embodiment 9].

In some cases of any one of Embodiments 1-9, at least 50 vol % of the particulate aerogel material is made up of particles having a maximum cross-sectional dimension of less than or equal to 1 centimeter [Embodiment 10].

In some cases of any one of Embodiments 1-9, at least 50 vol % of the particulate aerogel material is made up of particles having a maximum cross-sectional dimension of greater than or equal to 50 nanometers and less than or equal to 1 centimeter [Embodiment 11].

In some cases of any one of Embodiments 1-11, the particulate aerogel material comprises inorganic oxide aerogel [Embodiment 12].

In some cases of Embodiment 12, the inorganic oxide aerogel comprises an oxide of silicon, aluminum, titanium, hafnium, zirconium, chromium, niobium, tantalum, iron, vanadium, neodymium, samarium, holmium, zinc, magnesium, calcium, and/or erbium [Embodiment 13].

In some cases of Embodiment 12, the inorganic oxide aerogel comprises an oxide of silicon [Embodiment 14].

In some cases of any one of Embodiments 1-14, the particulate aerogel material exhibits a BET surface area of greater than or equal to 5 m2/g and less than or equal to 4000 m2/g [Embodiment 15].

In some cases of any one of Embodiments 1-15, when the particulate aerogel material is submerged under water for 24 hours at 25° C., the particulate aerogel material uptakes a mass of water within the outer boundaries of the particulate aerogel material of less than or equal to 30% of the dry mass of the particulate aerogel material just prior to submerging in the water [Embodiment 16].

In some cases of any one of Embodiments 1-16, the particulate aerogel material exhibits an optical transmission of greater than or equal to 5% at 635 nm [Embodiment 17].

In some cases of any one of Embodiments 1-17, when the particulate aerogel material is submerged under oil for 24 hours at 25° C., the particulate aerogel material uptakes a mass of oil within the outer boundaries of the particulate of greater than or equal to 20% of the dry mass of the particulate aerogel material just prior to submerging in the oil [Embodiment 18].

In some cases of any one of Embodiments 1-18, the particulate aerogel material will fracture when subjected to a pressure of less than 1 N/cm2 [Embodiment 19].

In some cases of any one of Embodiments 1-19, the particulate aerogel material exhibits a BJH pore volume of greater than or equal to 0.05 cm3/g and less than or equal to 5 cm3/g [Embodiment 20].

In some cases of any one of Embodiments 1-20, friction between the human skin and the solid surface, when the particulate aerogel material is present between the human skin and the solid surface, is higher than it would be under otherwise identical conditions without the particulate aerogel material [Embodiment 21].

In some cases of any one of Embodiments 1-21, the solid surface is part of a gripable object [Embodiment 22].

In some cases of any one of Embodiments 1-21, the solid surface is part of a handle [Embodiment 23].

In some cases of any one of Embodiments 1-21, the solid surface is part of a grip [Embodiment 24].

In some cases of any one of Embodiments 1-24, the solid surface is part of a musical instrument [Embodiment 25].

In some cases of Embodiment 25, the musical instrument is a guitar, piano, violin, viola, cello, bass, organ, keytar, accordion, keyboard, concertina, ukulele, melodica, lute, harmonica, recorder, bagpipe, tuba, trumpet, French horn, trombone, saxophone, clarinet, oboe, flute, sousaphone, flugelhorn, cornet, euphonium, or bells [Embodiment 26].

In some cases of any one of Embodiments 1-24, the solid surface is part of a musical instrument accessory [Embodiment 27].

In some cases of Embodiment 27, the musical instrument accessory is a guitar pick, drumstick, violin bow, viola bow, cello bow, bass bow, xylophone mallet, or conductor's wand [Embodiment 28].

In some cases of any one of Embodiments 1-24, the solid surface is part of a piece of sports equipment [Embodiment 29].

In some cases of Embodiment 29, the sports equipment is a baseball bat, baseball glove, racket (e.g., tennis racket, badminton racket), golf club, dart, arrow, bow, pole (e.g., flagpole), paddle, mast, frisbee, hammer, oar, whip, lasso, sword, javelin, shotput, discus, foil, sabre, epee, lacrosse stick, hockey stick, field hockey stick, parasail, wakeboard, paddleboard, squash racket, jai alai cesta, curling broom, curling stone, hurling stick, cricket bat, ski pole, pompom, boxing glove, horse reins, fishing pole, fishing net, jet ski, snowmobile, pool cue, sled, air hockey puck, table tennis paddle, skateboard, polo mallet, wetsuit, or softball bat [Embodiment 30].

In some cases of any one of Embodiments 1-24, the solid surface is part of a ball [Embodiment 31].

In some cases of Embodiment 31, the ball is a baseball, basketball, football, rugby ball, softball, racquetball, dodgeball, volleyball, tetherball, kickball, whiffle ball, lacrosse ball, squash ball, handball, spaldeen, juggling ball, cricket ball, bowling ball, golf ball, water polo ball, or pickle ball [Embodiment 32].

In some cases of any one of Embodiments 1-24, the solid surface is part of a handlebar [Embodiment 33].

In some cases of Embodiment 33, the handlebar is part of a bicycle (e.g., an electric bicycle), a motorcycle, a scooter (e.g., an electric scooter), a dirt bike, a motocross bike, a mountain bike, a snowmobile, a jet ski, or a glider [Embodiment 34].

In some cases of any one of Embodiments 1-24, the solid surface is part of a steering wheel [Embodiment 35].

In some cases of Embodiment 35, the steering wheel is part of a car, truck, four-wheeler, monster truck, or boat [Embodiment 36].

In some cases of any one of Embodiments 1-24, the solid surface is part of a rock [Embodiment 37].

In some cases of Embodiment 37, the rock is a synthetic rock or a natural rock (e.g., a mountain) [Embodiment 38].

In some cases of any one of Embodiments 1-24, the solid surface is part of a mat [Embodiment 39].

In some cases of Embodiment 39, the mat is a wrestling mat or a gymnastics mat [Embodiment 40].

In some cases of any one of Embodiments 1-24, the solid surface is part of a tool [Embodiment 41].

In some cases of Embodiment 41, the tool is a power drill, screwdriver, wrench, hammer, crowbar, saw, shovel, pitchfork, hoe, spade, or pick [Embodiment 42].

In some cases of any one of Embodiments 1-24, the solid surface is part of a video game controller [Embodiment 43].

In some cases of Embodiment 43, the video game controller is a mouse, keyboard, joystick, video game console controller, or video game console [Embodiment 44].

In some cases of any one of Embodiments 1-24, the solid surface is part of a firearm [Embodiment 45].

In some cases of Embodiment 45, the firearm is a handgun, rifle, machine gun, automatic weapon, semi-automatic weapon, revolver, or shotgun [Embodiment 46].

In some cases of any one of Embodiments 1-24, the solid surface is part of a piece of weightlifting equipment [Embodiment 47].

In some cases of Embodiment 47, the weightlifting equipment is a barbell, dumbbell, kettle bell, pull up bar, atlas stone, sandbag, yoke, farmers walk handle, carpet sled, log bar, or ez-curl bar [Embodiment 48].

In some cases of any one of Embodiments 1-24, the solid surface is part of a piece of gymnastics equipment [Embodiment 49].

In some cases of Embodiment 49, the piece of gymnastics equipment is uneven bars, parallel bars, rings, balance beam, trapeze, baton, trampoline, vault, pommel horse, or horizontal bar [Embodiment 50].

In some cases of any one of Embodiments 1-24, the solid surface is part of a door knob, helmet, other human skin, helicopter, rope, ladder, camera, wood, metal, torch, plastic, ceramic, composite, shoe, glove, sock, chain, microphone, cardboard box, Styrofoam box, cooler, umbrella, smartphone, computer, tablet, furniture, door, video camera, boom mic, switch, parachute, hot air balloon, katana, nunchaku, sai, shuriken, taser, spray can, megaphone, face, wall, window, boot, crutches, walker, cane, backpack, shopping bag, disk, tray, another human, animal, wheelchair, knob, button, directional pad, floor, or ground [Embodiment 51].

In some cases of any one of Embodiments 1-51, the solid surface is not human skin [Embodiment 52].

In some aspects, articles or kits are provided. In some embodiments, the article or kit comprises: a flexible container; and a particulate aerogel material within the container; wherein: at least a portion of a boundary of the container is porous and permits transport of the particulate aerogel through the porous boundary upon application of force to the flexible container [Embodiment 53].

In some cases of Embodiment 53, the flexible container has a volume of less than or equal to 5000 cm3, less than or equal to 2000 cm3, or less than or equal to 1000 cm3 [Embodiment 54].

In some cases of Embodiment 53, the flexible container has a volume such that the container occupies a footprint of at least 100 cm2 when a pressure of 100 N/cm2 is applied to the container [Embodiment 55].

In some embodiments, the article or kit comprises: a container; and particulate aerogel material within the container; wherein the container comprises a plurality of openings through which the particulate hydrophobic aerogel material can be transported [Embodiment 56].

In some cases of Embodiment 56, the plurality of openings is within a lid that is removable from the remainder of the container [Embodiment 57].

In some cases of Embodiment 56, the plurality of openings is within a wall of the container [Embodiment 58].

In some cases of Embodiment 56, the particulate aerogel material can leave the container when the container is inverted [Embodiment 59].

In some cases of any one of Embodiments 53-59, the particulate aerogel material can leave the container when a pressure of less than 100 N/cm2 is applied to the container [Embodiment 60].

In some aspects, materials are provided. In some embodiments, the material comprises: a liquid; and particulate aerogel material dispersed within the liquid [Embodiment 61].

In some cases of Embodiment 61, the material is a lotion [Embodiment 62].

In some cases of Embodiment 61, the material is a paste [Embodiment 63].

In some cases of Embodiment 61, the liquid has a vapor pressure of at least 0.025 atm at STP [Embodiment 64].

In some aspects, articles or kits are provided. In some embodiments, the article or kit comprises a liquid; and particulate aerogel material; wherein, when the liquid and the particulate aerogel material are combined, the particulate aerogel material and the liquid form a combination that enhances friction between human skin and solid surfaces [Embodiment 65].

In some cases of Embodiment 65, the combination is a lotion [Embodiment 66].

In some cases of Embodiment 65, the combination is a paste [Embodiment 67].

In some cases of Embodiment 65, the liquid has a vapor pressure of at least 0.025 atm at STP [Embodiment 68].

In some embodiments, the combination comprises human skin; particulate aerogel material in contact with the human skin; and a solid surface in contact with the particulate aerogel material [Embodiment 69].

In some cases of Embodiment 69, the particulate aerogel material is part of a layer [Embodiment 70].

In some cases of Embodiment 70, the average layer thickness is greater than or equal to 50 nanometers, and less than or equal to 1 millimeter [Embodiment 71].

In some aspects, articles or kits are provided. In some embodiments, the article comprises: a fibrous matrix; and particulate aerogel material associated with the fibrous matrix; wherein the combination of the fibrous matrix and the particulate aerogel material is in the form of a sheet [Embodiment 72].

In some cases of Embodiment 72, the sheet is in the form of a roll [Embodiment 73].

In some cases of Embodiment 73, the roll comprises perforations between portions of the sheet [Embodiment 74].

In some aspects, articles or kits are provided. In some embodiments, the article or kit comprises a container; and a plurality of sheets within the container; wherein each of the sheets comprises: a fibrous matrix; and particulate aerogel material associated with the fibrous matrix [Embodiment 75].

In some cases of Embodiment 75, the particulate aerogel material is present within the bulk of the fibrous matrix [Embodiment 76].

In some cases of Embodiment 75, the particulate aerogel material is present on at least one external surface of the fibrous matrix [Embodiment 77].

In some cases of Embodiment 75, at least one dimension of the sheet is greater than or equal to 100 micrometers and less than or equal to 1 millimeter [Embodiment 78].

In some cases of any one of Embodiments 53-78, the particulate aerogel material comprises inorganic oxide aerogel [Embodiment 79].

In some cases of Embodiment 79, the inorganic oxide aerogel comprises an oxide of silicon, aluminum, titanium, hafnium, zirconium, chromium, niobium, tantalum, iron, vanadium, neodymium, samarium, holmium, zinc, magnesium, calcium, and/or erbium [Embodiment 80].

In some cases of any one of Embodiments 65-80, the solid surface is part of a gripable object [Embodiment 81].

In some cases of any one of Embodiments 65-81, the solid surface is part of a handle [Embodiment 82].

In some cases of any one of Embodiments 65-82, the solid surface is part of a grip [Embodiment 83].

In some cases of any one of Embodiments 65-83, the solid surface is part of a musical instrument [Embodiment 84].

In some cases of Embodiment 84, the musical instrument is a guitar, piano, violin, viola, cello, bass, organ, keytar, accordion, keyboard, concertina, ukulele, melodica, lute, harmonica, recorder, bagpipe, tuba, trumpet, French horn, trombone, saxophone, clarinet, oboe, flute, sousaphone, flugelhorn, cornet, euphonium, or bells [Embodiment 85].

In some cases of any one of Embodiments 65-83, the solid surface is part of a musical instrument accessory [Embodiment 86].

In some cases of Embodiment 86, the musical instrument accessory is a guitar pick, drumstick, violin bow, viola bow, cello bow, bass bow, xylophone mallet, or conductor's wand [Embodiment 87].

In some cases of any one of Embodiments 65-83, the solid surface is part of a piece sports equipment [Embodiment 88].

In some cases of Embodiment 88, the sports equipment is baseball bat, baseball glove, tennis racket, badminton racket, racket, golf club, dart, arrow, bow, flagpole, paddle, pole, mast, frisbee, hammer, oar, whip, lasso, sword, javelin, shotput, discus, foil, sabre, epee, lacrosse stick, hockey stick, field hockey stick, parasail, wakeboard, paddleboard, squash racket, jai alai cesta, curling broom, curling stone, hurling stick, cricket bat, ski pole, pompom, boxing glove, horse reins, fishing pole, fishing net, jet ski, snowmobile, pool cue, sled, air hockey puck, table tennis paddle, skateboard, polo mallet, gi, wetsuit, or softball bat [Embodiment 89].

In some cases of any one of Embodiments 65-83, the solid surface is part of a ball [Embodiment 90].

In some cases of Embodiment 90, the ball is a baseball, basketball, football, rugby ball, softball, racquetball, dodgeball, volleyball, tetherball, kickball, whiffle ball, lacrosse ball, squash ball, handball, spaldeen, juggling ball, cricket ball, bowling ball, golf ball, water polo ball, or pickle ball [Embodiment 91].

In some cases of any one of Embodiments 65-83, the solid surface is part of a handlebar [Embodiment 92].

In some cases of Embodiment 92, the handlebar is part of a bicycle, motorcycle, electric bicycle, scooter (e.g., razor scooter, electric scooter), dirt bike, motocross bike, mountain bike, snowmobile, jet ski, or glider [Embodiment 93].

In some cases of any one of Embodiments 65-83, the solid surface is part of a steering wheel [Embodiment 94].

In some cases of Embodiment 94, the steering wheel is part of a car, truck, four-wheeler, monster truck, or boat [Embodiment 95].

In some cases of any one of Embodiments 65-83, the solid surface is part of a rock [Embodiment 96].

In some cases of Embodiment 96, the rock is a synthetic rock or natural rock (e.g., a mountain) [Embodiment 97].

In some cases of any one of Embodiments 65-83, the solid surface is part of a mat [Embodiment 98].

In some cases of Embodiment 98, the mat is a wrestling mat or gymnastics mat [Embodiment 99].

In some cases of any one of Embodiments 65-83, the solid surface is part of a tool [Embodiment 100].

In some cases of Embodiment 100, the tool is a power drill, screwdriver, wrench, hammer, crowbar, saw, shovel, pitchfork, hoe, spade, or pick [Embodiment 101].

In some cases of any one of Embodiments 65-83, the solid surface is part of a video game controller [Embodiment 102].

In some cases of Embodiment 102, the video game controller is a mouse, keyboard, joystick, video game console controller, or video game console [Embodiment 103].

In some cases of any one of Embodiments 65-83, the solid surface is part of a firearm [Embodiment 104].

In some cases of Embodiment 104, the firearm is a handgun, rifle, machine gun, automatic weapon, semi-automatic weapon, revolver, or shotgun [Embodiment 105].

In some cases of any one of Embodiments 65-83, the solid surface is part of a piece of weightlifting equipment [Embodiment 106].

In some cases of Embodiment 106, the weightlifting equipment is a barbell, dumbbell, kettle bell, pull up bar, atlas stone, sandbag, yoke, farmers walk handle, carpet sled, log bar, or ez-curl bar [Embodiment 107].

In some cases of any one of Embodiments 65-83, the solid surface is part of a piece of gymnastics equipment [Embodiment 108].

In some cases of Embodiment 108, the piece of gymnastics equipment is uneven bars, parallel bars, rings, balance beam, trapeze, baton, trampoline, vault, pommel horse, or horizontal bar [Embodiment 109].

In some cases of any one of Embodiments 65-83, the solid surface is part of a door knob, helmet, other human skin, helicopter, rope, ladder, camera, wood, metal, torch, plastic, ceramic, composite, shoe, glove, sock, chain, microphone, cardboard box, Styrofoam box, cooler, umbrella, smartphone, computer, tablet, furniture, door, video camera, boom mic, switch, parachute, hot air balloon, katana, nunchaku, sai, shuriken, taser, spray can, megaphone, face, wall, window, boot, crutches, walker, cane, backpack, shopping bag, disk, tray, another human, animal, wheelchair, knob, button, or directional pad [Embodiment 110].

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A grip enhancement kit, comprising:
   particulate aerogel material; and
   a container adapted to contain the particulate aerogel material;
   wherein the particulate aerogel material is contained within the container;
   wherein the particulate aerogel material is not dispersed in a liquid; and
   wherein the container comprises a plurality of openings through which the particulate aerogel material can be transported.

2. The kit of claim 1, wherein the plurality of openings is within a lid that is removable from the remainder of the container.

3. The kit of claim 1, wherein the plurality of openings is within a wall of the container.

4. The kit of claim 1, wherein the particulate aerogel material can pass through the plurality of openings when the container is inverted.

5. The kit of claim 1, wherein the plurality of openings comprises one opening.

6. The kit of claim 1, wherein the density of the plurality of openings comprises at least 1/cm2, at least 2/cm2, at least 5/cm2, at least 10/cm2, at least 50/cm2, or more than 50/cm2.

7. The kit of claim 1, wherein the particulate aerogel material can pass through the plurality of openings when a pressure of less than 100 N/cm2 is applied to the container.

8. The kit of claim 1, further comprising written instructions for at least one of the use, application, administration, or storage of the particulate aerogel material.

9. The kit of claim 8, wherein the written instructions comprise one of a bar code or a quick response code.

10. The kit of claim 1, wherein, when the particulate aerogel material is applied between human skin and a solid surface, the friction between the human skin and the solid surface is higher than it would be without the particulate aerogel material and under otherwise identical conditions.

11. A grip enhancement kit, comprising:
    a plurality of dry aerogel particles; and
    a container adapted to contain the dry aerogel particles;
    wherein the dry aerogel particles are contained within the container; and
    wherein at least 50 vol % of the dry aerogel particles have a maximum cross-sectional dimension of greater than or equal to 50 nanometers.

12. The kit of claim 11, wherein the container comprises a plurality of openings through which the aerogel particles can pass through.

13. The kit of claim 11, wherein the container comprises a flexible container.

14. The kit of claim 13, wherein the aerogel particles will fracture when subjected to a pressure of less than 1 N/cm2.

15. The kit of claim 14, wherein the container is adapted to allow the application of a crushing force to the aerogel particles contained within the container.

16. The kit of claim 11, wherein the average maximum cross-sectional dimension of the aerogel particles is less than or equal to 1 centimeter.

17. The kit of claim 11, wherein the aerogel particles comprise inorganic oxide aerogel.

18. The kit of claim 11, wherein the inorganic oxide aerogel comprises an oxide of silicon, aluminum, titanium, hafnium, zirconium, chromium, niobium, tantalum, iron, vanadium, neodymium, samarium, holmium, zinc, magnesium, calcium, and/or erbium.

19. The kit of claim 11, wherein the aerogel particles exhibit a BET surface area of greater than or equal to 5 m2/g and less than or equal to 4000 m2/g.

20. The kit of claim 11, wherein, when the aerogel particles are submerged under water for 24 hours at 25° C., the aerogel particles uptakes a mass of water within the outer boundaries of the aerogel particles of less than or equal to 30% of the dry mass of the aerogel particles just prior to submerging in the water.

21. The kit of claim 11, wherein the aerogel particles exhibit an optical transmission of greater than or equal to 5% at 635 nm.

22. The kit of claim 11, wherein, when the aerogel particles are submerged under oil for 24 hours at 25° C., the aerogel particles uptakes a mass of oil within the outer boundaries of the aerogel particles of greater than or equal to 20% of the dry mass of the aerogel particles just prior to submerging in the oil.

23. The kit of claim 11, wherein the aerogel particles exhibit a BJH pore volume of greater than or equal to 0.05 cm3/g and less than or equal to 5 cm3/g.

24. The kit of claim 11, wherein, when the aerogel particles are applied between human skin and a solid surface, the friction between the human skin and the solid surface is higher than it would be without the aerogel particles and under otherwise identical conditions.

25. The kit of claim 13, wherein the container comprises at least one of fabric, paper, plastic, or rubber.

26. The kit of claim 13, wherein at least a portion of a boundary of the container is porous and permits transport of the aerogel particles through the porous boundary upon application of force to the flexible container.

* * * * *